United States Patent
Song et al.

(10) Patent No.: US 12,291,531 B2
(45) Date of Patent: May 6, 2025

(54) MATRINE α-KETOAMINE COMPOUNDS, PREPARATION METHOD THEREFOR AND USE THEREOF

(71) Applicant: SHANGHAI XINGYE PHARMACEUTICAL TECHNOLOGY CO., LTD, Shanghai (CN)

(72) Inventors: Weibin Song, Shanghai (CN); Yanhui Liu, Shanghai (CN)

(73) Assignee: SHANGHAI XINGYE PHARMACEUTICAL TECHNOLOGY CO., LTD, Shanghai (CN)

( * ) Notice: Subject to any disclaimer, the term of this patent is extended or adjusted under 35 U.S.C. 154(b) by 1087 days.

(21) Appl. No.: 17/267,961

(22) PCT Filed: Aug. 14, 2019

(86) PCT No.: PCT/CN2019/100674
§ 371 (c)(1),
(2) Date: Feb. 11, 2021

(87) PCT Pub. No.: WO2020/035010
PCT Pub. Date: Feb. 20, 2020

(65) Prior Publication Data
US 2021/0221812 A1 Jul. 22, 2021

(30) Foreign Application Priority Data
Aug. 14, 2018 (CN) .......................... 201810918861.6

(51) Int. Cl.
*C07D 471/22* (2006.01)
*A61P 35/00* (2006.01)

(52) U.S. Cl.
CPC ............ *C07D 471/22* (2013.01); *A61P 35/00* (2018.01)

(58) Field of Classification Search
CPC .................................................... C07D 471/22
See application file for complete search history.

(56) References Cited

FOREIGN PATENT DOCUMENTS

| CN | 101704817 A | 5/2010 |
|---|---|---|
| CN | 104804000 A | 7/2015 |
| CN | 105884774 A | 8/2016 |
| CN | 105884775 A | 8/2016 |
| CN | 107286162 A | 10/2017 |
| CN | 108299435 A | 7/2018 |
| WO | 2011/134283 A1 | 11/2011 |

OTHER PUBLICATIONS

American Chemical Society. Chemical Abstract Service. RN 1676126-98-9. Entered into STN: Apr. 3, 2015. (Year: 2015).*
American Chemical Society. Chemical Abstract Service. RN 1643108-35-3. Entered into STN: Jan. 15, 2015. (Year: 2015).*
Gao et al., Design and synthesis of oxymatrine analogues overcoming drug resistance in hepatitis B virus through targeting host heat stress cognate 70. J Med Chem. Feb. 10, 2011;54(3):869-76.
International Search Report and Written Opinion for Application No. PCT/CN2019/100674, dated Oct. 31, 2019, 6 pages.

* cited by examiner

*Primary Examiner* — John S Kenyon
(74) *Attorney, Agent, or Firm* — McCarter & English, LLP; Wei Song

(57) ABSTRACT

The present invention disclosed a series of novel matrine α-ketoamine derivatives as shown in formula I, which could inhibit the overexpression of TNF-α and/or activate the immune killing function of the NK cells, thus could be used to treat autoimmune diseases, inflammatory diseases, neurodegenerative diseases and tumors mediated by the abnormal levels of TNF-α and/or NK cell dysfunction.

12 Claims, 1 Drawing Sheet

MATRINE α-KETOAMINE COMPOUNDS, PREPARATION METHOD THEREFOR AND USE THEREOF

CROSS-REFERENCE TO RELATED APPLICATIONS

This application is a U.S. national stage filing, under 35 U.S.C. § 371 (c), of International Application No. PCT/CN2019/100674, filed on Aug. 14, 2019, which claims priority to Chinese Patent Application No. 201810918861.6, filed on Aug. 14, 2018.

FIELD OF INVENTION

The invention belongs to the technical field of medicine and provides a class of matrine α-ketoamine derivatives as well as their pharmaceutically acceptable salts, which can inhibit the overexpression of TNF-α and/or activate the immune killing function of the NK cells. The invention also provides the preparation method and the use thereof for preventing and/or treating diseases such as autoimmune diseases, tumors, myelofibrosis and acute and chronic graft-versus-host disease, which are highly associated with the dysfunctions of TNF-α signaling pathway and/or the NK cells immune responses.

PRIOR ARTS

TNF-α (tumor necrosis factor-a): TNF-α is discovered in the 1970s, and recognized as a kind of proinflammatory cytokine which plays an important role in immune homeostasis, inflammation, and host defense. TNF-α is mainly secreted by activated monocytes, macrophages and T cells, and could activate the membrane receptors of caspase protease, JNK, and the transcription factor NF-κB, thus regulate a number of different biological processes, such as cell growth and apoptosis, tumor formation, immunity, inflammation and stress response, and so on. Uncontrolled activity of TNF-α or overproduction of TNF-α is associated with the pathology of various diseases, including but not limited to cancers and inflammatory diseases, such as systemic inflammatory response syndrome, inflammatory bowel disease, rheumatoid arthritis, neurodegenerative diseases (multiple sclerosis, Motor neuron disease, Alzheimer's disease, Parkinson), psoriasis, cerebral malaria, diabetes, osteoporosis, allograft rejection, multiple sclerosis, HBV, HCV and HIV, etc. (Brenner D. et. al. Regulation of tumor necrosis factor signaling: live or let die. *Nat Rev Immunol.* 2015, 15, 362.). Therefore, reducing the level of TNF-α, or regulating the activity of TNF-α is a promising strategy in treating many immunological, inflammatory, and malignant diseases.

Natural killer (NK) cells are a type of large granula lymphocytes for innate immune defense without the need of prior sensitization comparing with T and B cells. NK cells constitute about 10~15% of lymphocytes in the peripheral blood of healthy humans and serve as critical sentinels protecting against tumor and virus-infected cells. Mature human NK-cells refer to CD3X D56+ lymphocytes and can be divided into $CD56^{dim}$ (~90%) and $CD56^{bright}$ (~10%) NK-cell subsets according to their relative density of CD56 surface expression. $CD56^{dim}$ NK cells, mainly distributed in the peripheral blood and spleen, have little proliferative capacity and can produce negligible amounts of perforin once activated, yet are highly cytotoxic at rest, in contrast, $CD56^{bright}$ NK cells proliferate and secrete abundant cytokines, such as IFN-γ, IL-12, IL-15 AND 18 etc., but display minimal cytotoxic activity at rest. NK cells can recognize the target cells and kill tumor and virus spontaneously without MHC restriction or presensitization, and antibody dependent. Although the NK cell immune responses display broad spectrum antitumor effect, the immune checkpoints or switches of NK cells can also be suppressed by tumor. For example, the tumor cells can generate some ligands and inhibit NK cell immune checkpoints, such as killer cell immunoglobulin like receptors (KIRs), C-type lectin receptors (NKG2a/CD94), leukocyte immunoglobulin like receptors (Lilrs), and the well-known immune checkpoint receptors PD-1, Tim-3, LAG-3 and Tigit, which enable the tumor to escape from the host immune system. Thus, the development of new method to activate the tumor-suppressed immune responses of NK cells leading to recognize and kill tumor cells is highly desirable.

Matrine components refer to the quinolizidine alkaloids such as matrine, oxymatrine, sophoridine, sophocarpine and sophoramine, as well as their analogues that are isolated from genus *Sophora* of Traditional Chinese Medicine (TCM) such as radix *Sophorae flavescentis, Sophora alopecuroides, Sophora tonkinensis* etc. Recent studies have shown that matrine components could activate the tumor-suppressed NK cells recognize and kill tumor cells (XZ Lu. et. al. Matrine increases NKG2D ligand ULBP2 in K562 cells via inhibiting JAK/STAT3 pathway: a potential mechanism underlying the immunotherapy of matrine in leukemia. *Am J Transl Res.* 2015, 7, 1838). However, these matrine components showed weak potency and poor druggability. For example, the effective dose for TNF-α, IL-2, IL-y and other inflammatory cytokines inhibiting need 0.5 M concentration, while the toxic dose for the normal cells only at the 1~2 M concentration. Obviously, the narrow drug safety window limits their clinical therapeutic effect and application for the treatment of tumor and immune diseases. Therefore, matrine derivatives being of improved structures are urgently desired to optimize its performance of potency and safety in the field.

CONTENT OF THE PRESENT INVENTION

A general object of the present invention is to provide a new series of matrine a-ketoamine compounds.

A more specific object of the present invention is to provide a method for preparing these matrine α-ketoamine derivatives.

Another object of the present invention is to provide the use of these matrine a-ketoamine compounds, which can regulate the production or activity of TNF-α and activate the immune-suppressed NK cells, thus can be effectively used for treating cancers and inflammatory diseases.

The present invention provides a new type of matrine α-ketoamine derivatives represented by general formula (I), a pharmaceutically acceptable salt, a solvate, a polymorph, a stereoisomer, an isotopic or a metabolite compound thereof.

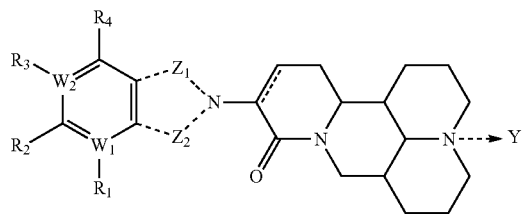

(I)

In the general formula (I), each of $R_1$, $R_2$, $R_3$ and $R_4$ is independently selected from H, D, halogen, hydroxyl, amino, nitro, cyano, carboxyl, mercapto, $(C_0-C_8)$ alkoxyformyl $C_1-C_8$ alkoxyl, $C_1-C_8$ alkanesulfonyl, $(C_1-C_8)$ alkanesulfonamido, $(C_0-C_8)$ alkylaminosulfonyl, $(C_1-C_8)$ alkyl, halo $(C_1-C_8)$ alkyl, halo $(C_1-C_8)$ alkoxyl, $(C_0-C_8)$ alkylethynyl, $(C_1-C_8)$ alkoxyl, $(C_1-C_8)$ alkylacyloxy, $(C_1-C_8)$ alkoxyl $(C_1-C_8)$ alkoxyl, $(C_1-C_8)$ alkoxyl $(C_1-C_8)$ alkyl, $(C_1-C_8)$ alkylamino, $(C_0-C_8)$ alkylamino $(C_1-C_8)$ alkyl, aryl, aryl $(C_1-C_8)$ alkylamino $(C_1-C_8)$ alkyl, amidino, guanidino, arylsulfonamido, arylaminosulfonyl, benzoyl, aryl $(C_1-C_8)$ alkylamino, aryl $(C_1-C_8)$ alkylamido, $(C_1-C_8)$ alkoxyformyl, $(C_1-C_8)$ alkylamido, $(C_1-C_8)$ alkylamino, $(C_0-C_8)$ alkylamino selenyl, $(C_0-C_8)$ alkylamino formamido, $(C_0-C_8)$ alkylamino formyl, $(C_1-C_8)$ alkylaminoformyloxyl, arylaminoformamido, arylaminoformyl, aryl $(C_0-C_8)$ alkylaminoformyl, arylaminoformyloxyl, piperidinyl, piperazinyl, morpholinyl, pyrrolyl, pyrazolyl, imidazolyl, pyridyl, pyrazinyl, quinolinyl, pyrimidinyl, pyrimidinylamino, thiazolyl, thienyl, furanyl, pyrrolyl or absent; wherein, the aryl groups of $R_1$, $R_2$, $R_3$ and $R_4$ described are phenyl or are phenyl which independently substituted with 1-4 halogen, hydroxy, nitro, cyano, amino, trifluoromethyl, carboxyl, $(C_1-C_8)$ alkanesulfonamido, $(C_1-C_8)$ alkyl, halo $(C_1-C_8)$ alkoxyl, $(C_1-C_8)$ alkoxyl groups;

X is, S or O;

Y is, O or not exist;

$Z_1$ and/or $Z_2$ are independently selected from $SO_2$, C=O, C=S, C=$NR_5$, N=$CR_6$, COCO, $CH_2CO$, $CH(CH_3)CO$, $CH_2$, $CH(CH_3)_2$, $CH_2CH(CH_3)_2$, H, D or not exist; wherein, $R_5$ is selected from H, $(C_1-C_8)$ alkoxyl; $R_6$ is selected from H, $(C_1-C_8)$ alkyl;

$W_1$ and/or $W_2$ are independently selected from N or C; wherein, when $W_1$ and/or $W_2$ is C, $R_1$ and $R_3$ are not exist;

Where bonds represented by "-----" is chemical bond or not exist.

Preferably, the present invention provides a series of novel compounds represented by formula (I-a) and (I-b), as well as a pharmaceutically acceptable salt, a solvate, a polymorph, a stereoisomer, an isotopic or a metabolite compound thereof.

Preferably, the present invention provides a series of compounds represented by formula (I-a), (I-b), (I-c), (I-d), and (I-e), as well as a pharmaceutically acceptable salt, a solvate, a polymorph, a stereoisomer, an isotopic or a metabolite compound thereof:

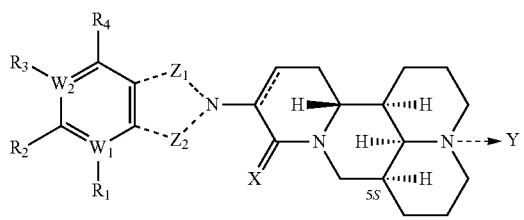

(I-a)

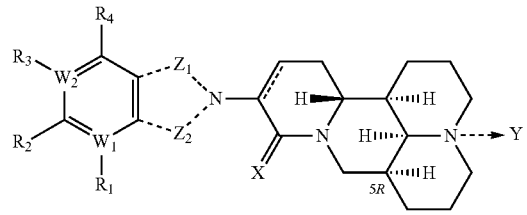

(I-b)

in the general formula (I-a) and (I-b), each of $R_1$, $R_2$, $R_3$ and $R_4$ is independently selected from H, D, halogen, hydroxyl, amino, nitro, cyano, carboxyl, mercapto, $(C_0-C_8)$ alkoxyformyl $C_1-C_8$ alkoxyl, $C_1-C_8$ alkanesulfonyl, $(C_1-C_8)$ alkanesulfonamido, $(C_0-C_8)$ alkylaminosulfonyl, $(C_1-C_8)$ alkyl, halo $(C_1-C_8)$ alkyl, halo $(C_1-C_8)$ alkoxyl, $(C_0-C_8)$ alkylethynyl, $(C_1-C_8)$ alkoxyl, $(C_1-C_8)$ alkylacyloxy, $(C_1-C_8)$ alkoxyl $(C_1-C_8)$ alkoxyl, $(C_1-C_8)$ alkoxyl $(C_1-C_8)$ alkyl, $(C_1-C_8)$ alkylamino, $(C_0-C_8)$ alkylamino $(C_1-C_8)$ alkyl, aryl, aryl $(C_1-C_8)$ alkylamino $(C_1-C_8)$ alkyl, amidino, guanidino, arylsulfonamido, arylaminosulfonyl, benzoyl, aryl $(C_1-C_8)$ alkylamino, aryl $(C_1-C_8)$ alkylamido, $(C_1-C_8)$ alkoxyformyl, $(C_1-C_8)$ alkylamido, $(C_1-C_8)$ alkylamino, $(C_0-C_8)$ alkylamino selenyl, $(C_0-C_8)$ alkylamino formamido, $(C_0-C_8)$ alkylamino formyl, $(C_1-C_8)$ alkylaminoformyloxyl, arylaminoformamido, arylaminoformyl, aryl $(C_0-C_8)$ alkylaminoformyl, arylaminoformyloxyl, piperidinyl, piperazinyl, morpholinyl, pyrrolyl, pyrazolyl, imidazolyl, pyridyl, pyrazinyl, quinolinyl, pyrimidinyl, pyrimidinylamino, thiazolyl, thienyl, furanyl, pyrrolyl or absent; wherein, the aryl groups of $R_1$, $R_2$, $R_3$ and $R_4$ described are phenyl or are phenyl which independently substituted with 1-4 halogen, hydroxy, nitro, cyano, amino, trifluoromethyl, carboxyl, $(C_1-C_8)$ alkanesulfonamido, $(C_1-C_8)$ alkyl, halo $(C_1-C_8)$ alkoxyl, $(C_1-C_8)$ alkoxyl groups;

X is, S or O;

Y is, O or not exist;

$Z_1$ and/or $Z_2$ are independently selected from $SO_2$, C=O, $CH_2CO$, $CH(CH_3)CO$, $CH_2$, $CH(CH_3)_2$, $CH_2CH(CH_3)_2$, H, D or not exist;

$W_1$ and/or $W_2$ are independently selected from N or C; wherein, when $W_1$ and/or $W_2$ is C, $R_1$ and $R_3$ are not exist;

where bonds represented by "-----" is chemical bond or not exist.

As used herein, the term "halogen" refers to fluorine, chlorine, bromine, and iodine.

As used herein, the term "halogenated" may have either a mono halogenated, or a poly halogenated.

As used herein, the term "alkanesulfonyl" refers to a linear or branched or cyclic saturated alkylsulfonyl group, and the cyclic saturated alkane described contains 3 to 8 carbon atoms.

As used herein, the term "alkanesulfonamido" refers to a linear or branched or cyclic saturated alkylsulfonamide group, and the cyclic saturated alkane described contains 3 to 8 carbon atoms.

As used herein, the term "alkylaminosulfonyl" refers to a N-monosubstituted or disubstituted linear or branched or cyclic saturated alkane aminosulfonyl group, and the cyclic saturated alkane described contains 3 to 8 carbon atoms.

As used herein, the term "alkylaminoformyl" refers to a N-monosubstituted or disubstituted linear or branched or cyclic saturated alkane aminoformyl group, and the cyclic saturated alkane described contains 3 to 8 carbon atoms.

As used herein, the term "alkane" refers to a linear or branched or cyclic saturated alkyl group, and the cyclic saturated alkane described contains 3 to 8 carbon atoms.

As used herein, the term "alkoxy" refers to a linear or branched or cyclic saturated alkoxyl group, and the cyclic saturated alkane described contains 3 to 8 carbon atoms.

As used herein, the term "alkylethynyl" refers to a linear or branched or cyclic saturated alkane ethynyl, and the cyclic saturated alkane described contains 3 to 8 carbon atoms.

As used herein, the term "alkylacyloxy" refers to a linear or branched or cyclic saturated alkane acyloxy group, and the cyclic saturated alkane described contains 3 to 8 carbon atoms.

As used herein, the term "alkylamino" refers to a N-monosubstituted or disubstituted linear or branched or cyclic saturated alkane amine, and the cyclic saturated alkane described contains 3 to 8 carbon atoms.

As used herein, the term "alkoxyformyl" refers to a linear or branched or cyclic saturated alkoxyformyl group, and the cyclic saturated alkane described contains 3 to 8 carbon atoms.

As used herein, the term "alkylamido" refers to a linear or branched or cyclic saturated alkane amido group, and the cyclic saturated alkane described contains 3 to 8 carbon atoms.

As used herein, the term "alkylaminoformamido" refers to a linear or branched or cyclic saturated alkane aminoformamido group, and the cyclic saturated alkane described contains 3 to 8 carbon atoms.

As used herein, the term "stereoisomers" refers to the chiral compounds that contain one or more stereocenters, the term "stereoisomer" herein including enantiomer, diastereoisomer.

As used herein, unless otherwise specified, the substituted attachment site of "piperazinyl, morpholinyl, pyrrolyl, pyrazolyl, pyrrolyl, imidazolyl, pyrimidylamino" groups are at the nitrogen atom.

As used herein, unless otherwise specified, the substituted attachment site of "pyridyl, pyrimidinyl, thiazolyl, thienyl, furanyl, pyrazinyl, quinolinyl" are at the carbon atom.

In the case where the compounds described in the present invention have stereoisomers, the stereoisomers include all stereoisomers of the compounds.

The present invention also includes deuterated compounds which refers to one or more of the hydrogen atoms in the compound is replaced by its heavier isotope deuterium.

As used herein, the term "metabolite" refers to an active substance produced after the chemical structure of a drug molecule changes in vivo, the active substance is generally a derivative of the aforementioned drug molecule, and also can be chemically modified.

As used herein and unless otherwise specified, the term "polymorph" refers to one or more than one kind(s) of crystal structure formed by the different arrangement of molecules in the lattice space when crystallizing.

As used herein, the term "solvate" refers to a crystal form of the compound having a structure of general formula (I), the pharmaceutically acceptable salt, the polymorph, the stereoisomer, the isotopic compound, the metabolite or the prodrug thereof, which further has one or more than one kind(s) of solvent molecule(s) incorporated into the crystal structure. The solvate may include a stoichiometric amount or a non stoichiometric amount of solvent, and the solvent molecule in the solvent may exist in an ordered or non ordered arrangement. The solvate containing a non stoichiometric amount of solvent molecules may be formed by losing at least one solvent molecule (but not all) from the solvate. In a particular embodiment, a solvate refers to a hydrate, which means the crystal of the compound further includes water molecule, and water is used as a solvent.

The compounds having a structure of general formula (I) in the present invention, the pharmaceutically acceptable salt, the solvate, the polymorph, the stereoisomer, the isotopic compound or the metabolite thereof, can contain one or more than one asymmetric centers ("stereoisomer"). As used herein, the term "stereoisomer" refers to all stereoisomers including enantiomer, diastereoisomer, epimer, endo-exo isomer, atropisomer, regioisomer, cis- and trans-isomer. The "stereoisomer" herein also includes "pure stereoisomer" and "enriched stereoisomer" or "racemic isomer" of the various aforementioned stereoisomers. These stereoisomers can be prepared according to an asymmetric synthesis process, or separated, purified, and enriched by a chiral separation process (including but not limited to thin layer chromatography, rotating chromatography, column chromatography, gas chromatography, high pressure liquid chromatography, etc.), as well as obtained by chiral separation by means of bonding (chemical binding etc.) or salifying (physical binding etc.) with other chiral compound(s).

As used herein, the term "pharmaceutically acceptable salt" refers to a non-toxic acid salt of the compounds of formula I. These salts can be prepared in situ during the final isolation and purification of compounds of general formula I, or can be synthesized by reacting appropriate organic or inorganic acids with basic functional groups, respectively. Examples of the salt include but are not limited to, acetate, adipate, alginate, citrate, aspartate, benzoate, benzenesulfonate, hydrogen sulfate, butyrate, camphor salt, camphor sulfonate, digluconate, cyclopentanepropionate, dodecyl sulfate, ethanesulfonate, glucoheptanoate, glyceryl phosphate, hemisulfate, heptanoate Salt, hexanoate, fumarate, hydrochloride, hydrobromide, hydroiodate, 2-hydroxyethanesulfonate, lactate, maleate, mesylate, nicotinate, 2-naphthylsulfonate, oxalate, paraben, pectate, thiocyanate, 3-phenylpropionate, picrate, pivalate, propionate, amber acid salt, sulfate, tartrate, thiocyanate, p-toluene sulfonate and undecanoate.

As used herein, the chemical bond connection mode of "S=O, SO$_2$, C=O, C=S, C=NR$_5$, NR$_6$=C, CH=CH, CH$_2$CO, COCO, CH$_2$, H, N" in the present invention of formula I-a and I-b meet the octahedral rule, for example, S=O refers to

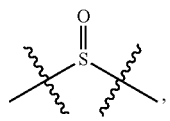 [SMILES: *S(*)=O]

C=O refers to

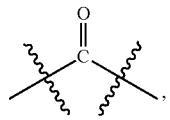 [SMILES: *C(*)=O]

CH=CH refers to
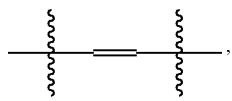
NR$_6$=C refers to
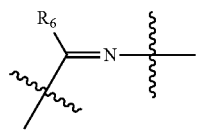
and/or
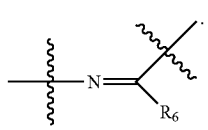
Some of the preferred novel matrine α-ketoamine compounds of the present invention are shown below. These examples are used for further explanation of the present invention only, and do not limit the scope of the present invention in any way.
M-3
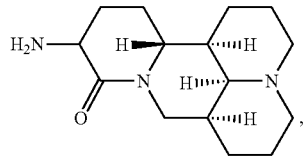
GJD01
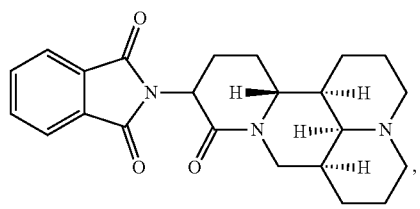
GJD02
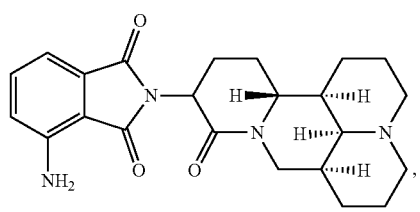
GJD03
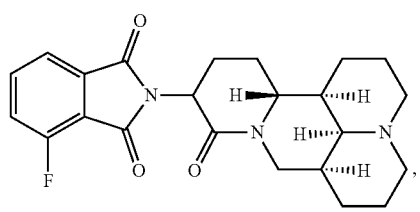
GJD04
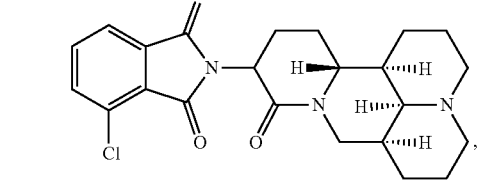
GJD05
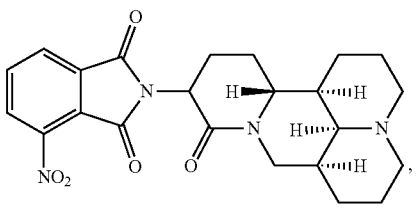
GJD06
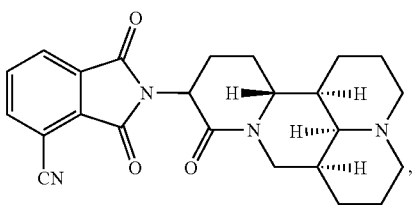
GJD07
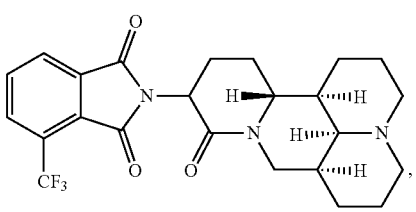
GJD08
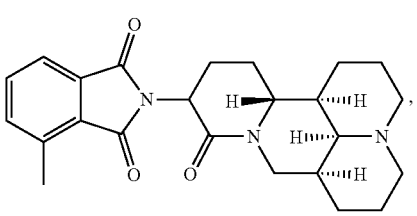
GJD09
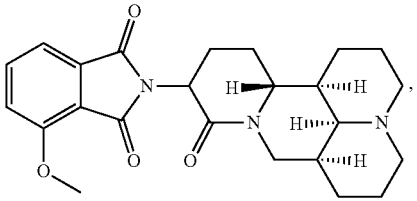
GJD10
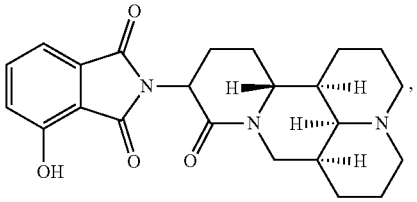

GJD11
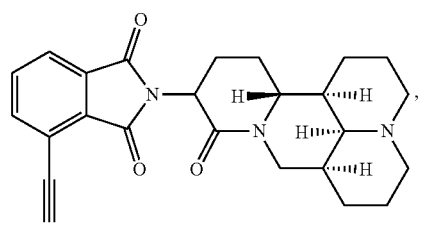
GLD12
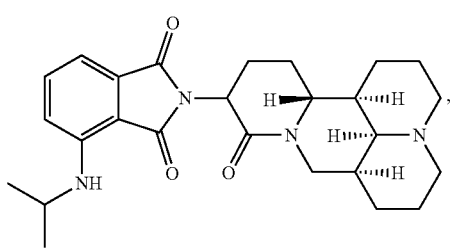
GJD13
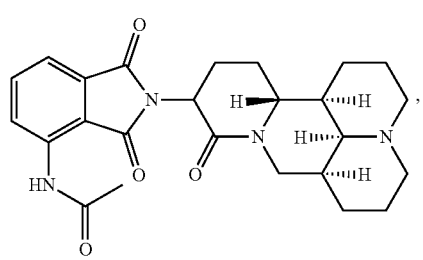
GJD14
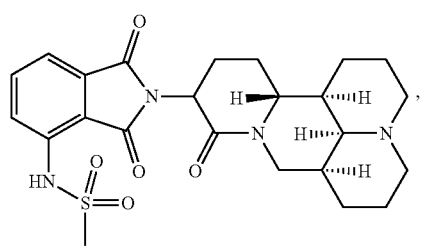
GJD15
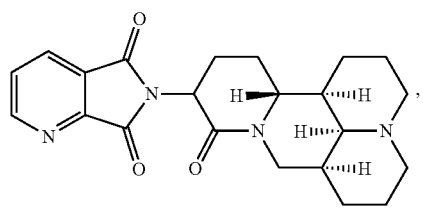
GJD16
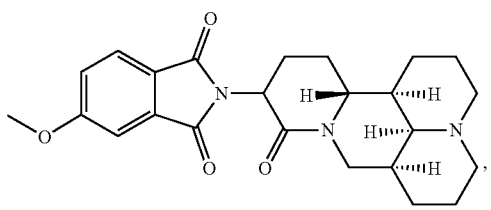
GJD17
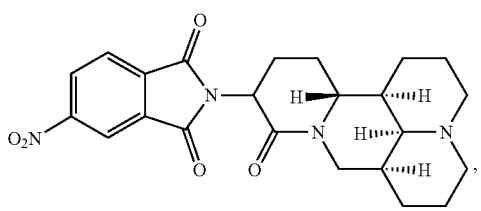
GJD18
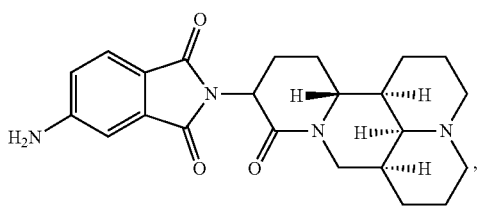
GJD19
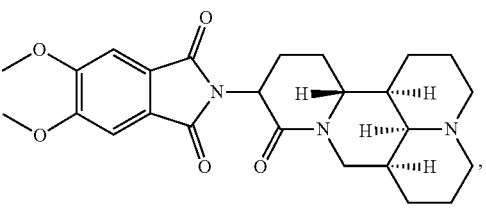
GJD20
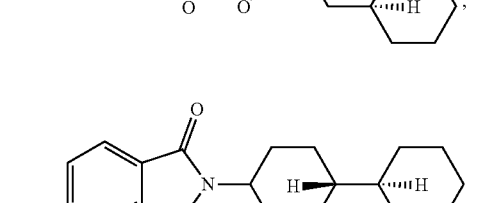
GJD21
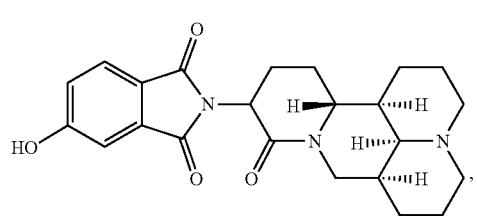
GJD22
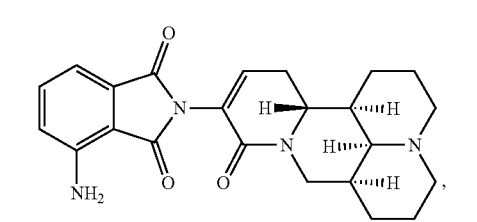
GJD23

GJD24, GJD25, GJD26, GJD27, GJD28, GJD29, GJD30, GJD31, GJD32, GJD33, GJD34, GJD35, GJD36, GJD37

GJD38
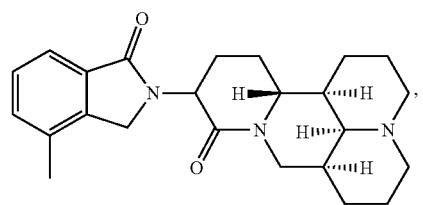
GJD39
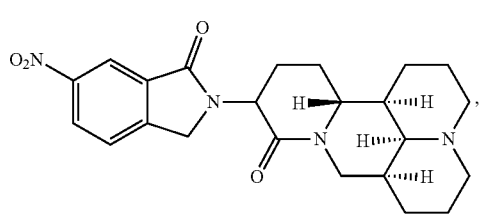
GJD40
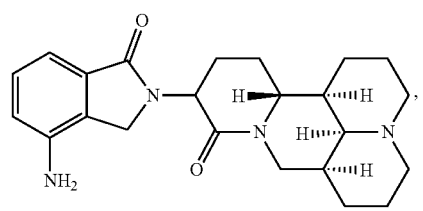
GJD41
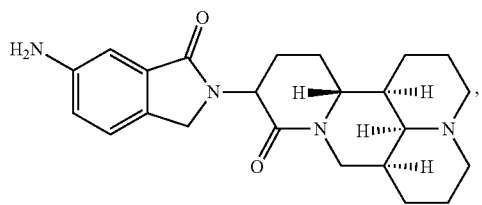
GJD42
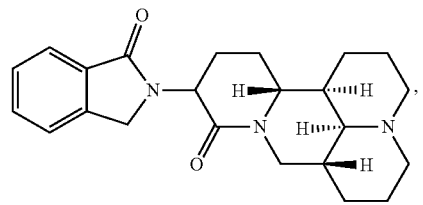
GJD43
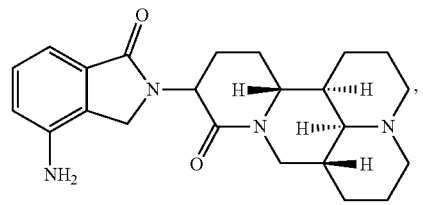
GJD44
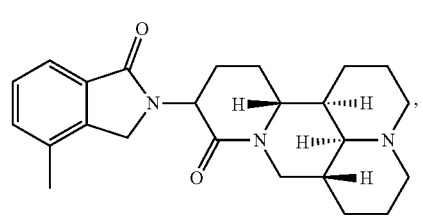
GJD45
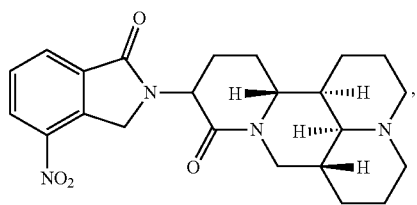
GJD46
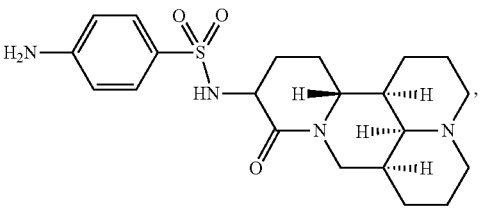
GJD47
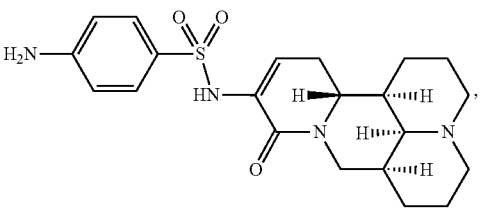
GJD48
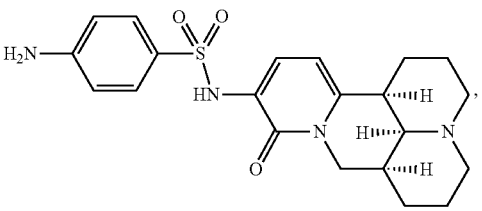
GJD49
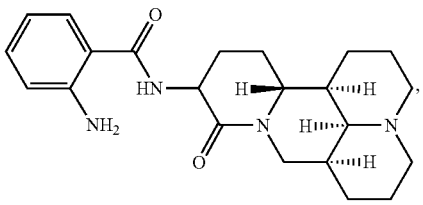
GJD50
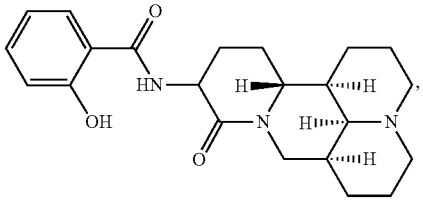
GJD51
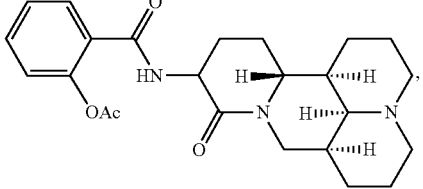

GJD52
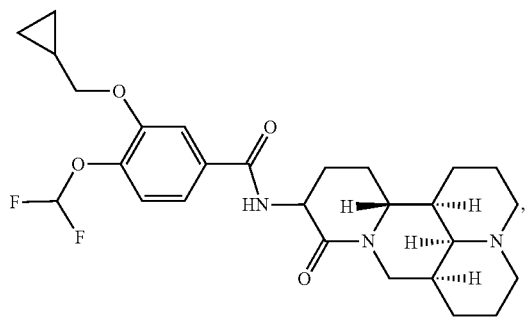
GJD53
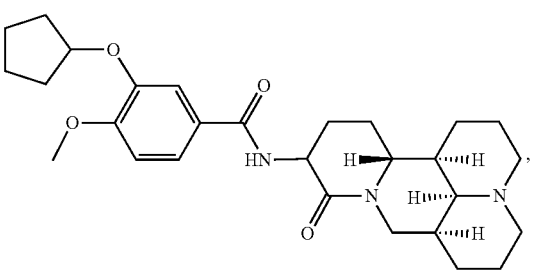
GJD54
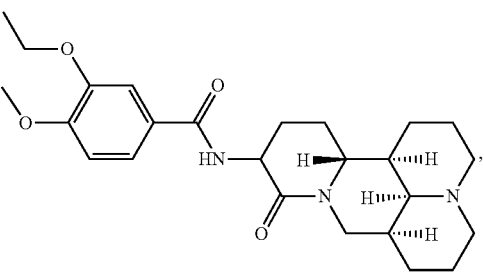
GJD55
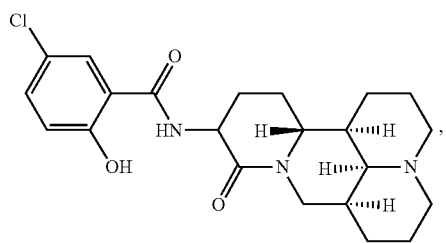
GJD56
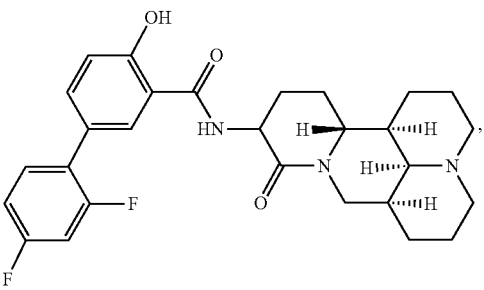
GJD57
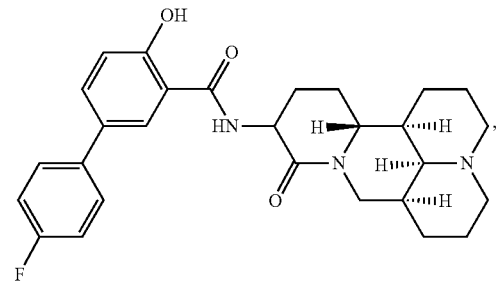
GJD58
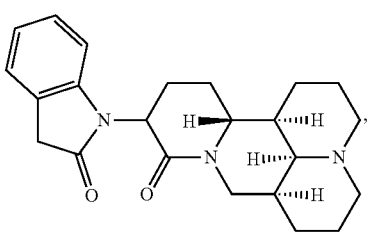
GJD59
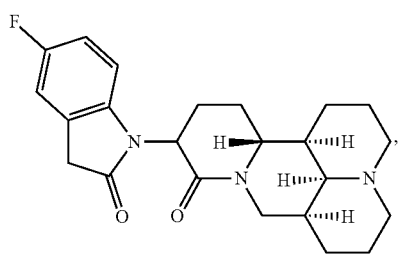
GJD60
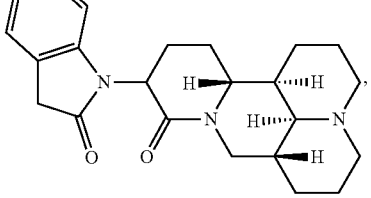
GJD61
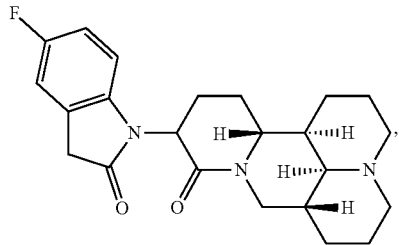
GJD62
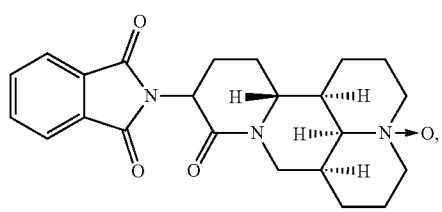

GJD63
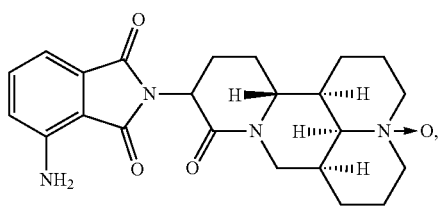

GJD64
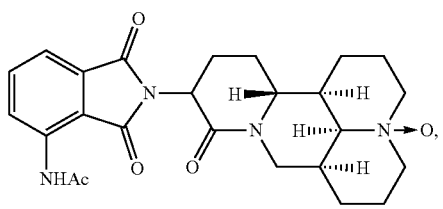

GJD65
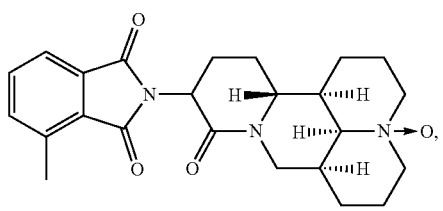

GJD66
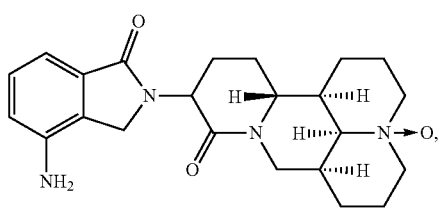

GJD67
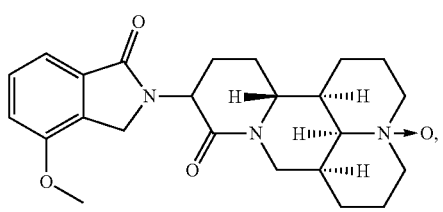

GJD68
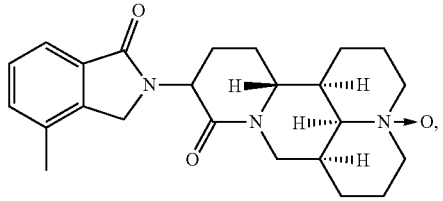

GJD69
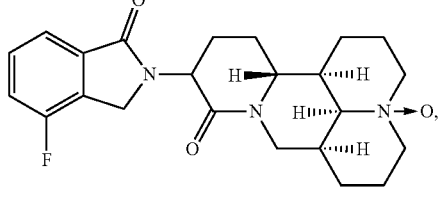

GJD70
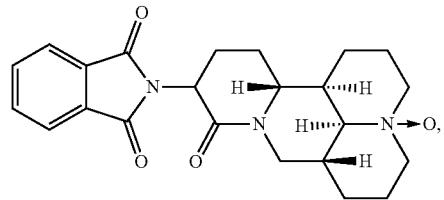

GJD71
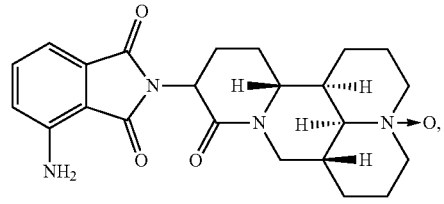

GJD72
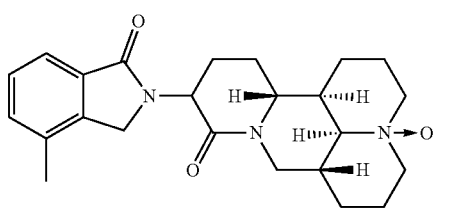 and/or

GJD73
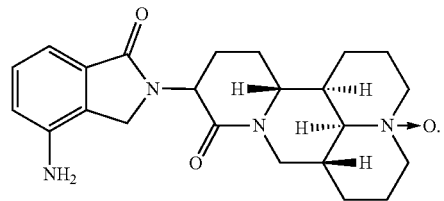

As is known to all, any stereocenter of the above-listed compounds that is not explicitly stated can be an absolute (R)- or(S)-configuration, or its racemic mixture. The present invention includes the racemic mixtures of the compounds, a mixture of any one of enrichment enantiomer, and any one of isolated enantiomer. For the scope of the present invention, the racemic mixture refers to a 50%:50% mixture of R and S enantiomer, and the isolated enantiomer should be understood as pure enantiomer (such as 100%) or a highly enriched mixture of certain enantiomer (purity ≥98%, ≥95%, ≥90%, ≥88%, ≥85%, ≥80%).

The present invention also provides a pharmaceutically acceptable salt of the above-mentioned novel selenium-containing isoxazolamines. The pharmaceutically acceptable salts of the present invention can be obtained using standard procedures as well known in the field, namely, the different salt can be obtained by reacting matrine alpha-ketoamine compounds with a suitable acid. The acid may be hydrochloric acid, hydrobromic acid, sulfuric acid, phosphoric acid, acetic acid, citric acid, oxalic acid, malonic acid, salicylic acid, malic acid, fumaric acid, succinic acid, mandelic acid, ascorbic acid, maleic acid, and tartaric acid, benzenesulfonic acid, methanesulfonic acid or isethionic acid.

According to the second object of the present invention, the methods for the preparation of matrine α-ketoamine compounds and/or their pharmaceutically acceptable salts are provided as follows.

The following abbreviations shall apply throughout the specification and examples:

Ac refers to acetyl group; AcOH refers to acetic acid. Base refers to organic or inorganic base; DMF refers to N,N-dimethylformamide; DBU refers to 1,8-diazabicycloundec-7-ene; DDQ dichlorodicyanobenzene quinone; EA refers to ethyl acetate. EtOH refers to ethanol. HA refers to organic or inorganic acids, such as hydrochloric acid, sulfuric acid, maleic acid, tartaric acid, etc. $H_2O_2$ refers to hydrogen peroxide; $I_2$ refers to iodine; LC-MS refers to high performance liquid chromatography-mass spectroscopy; $NaN_3$ refers to sodium azide; NMR refers to nuclear magnetic resonance chromatograph; TLC refers to thin layer chromatography; TMSI refers to trimethyliodosilane; TMEDA refers to N,N, N,N-tetramethylethylenediamine; V refers to solution volume.

The present compound of formula I can be prepared according to the following general method:

a) The synthesis route for preparing matrine α-ketoamine compounds represented by general formula I-a and I-b.

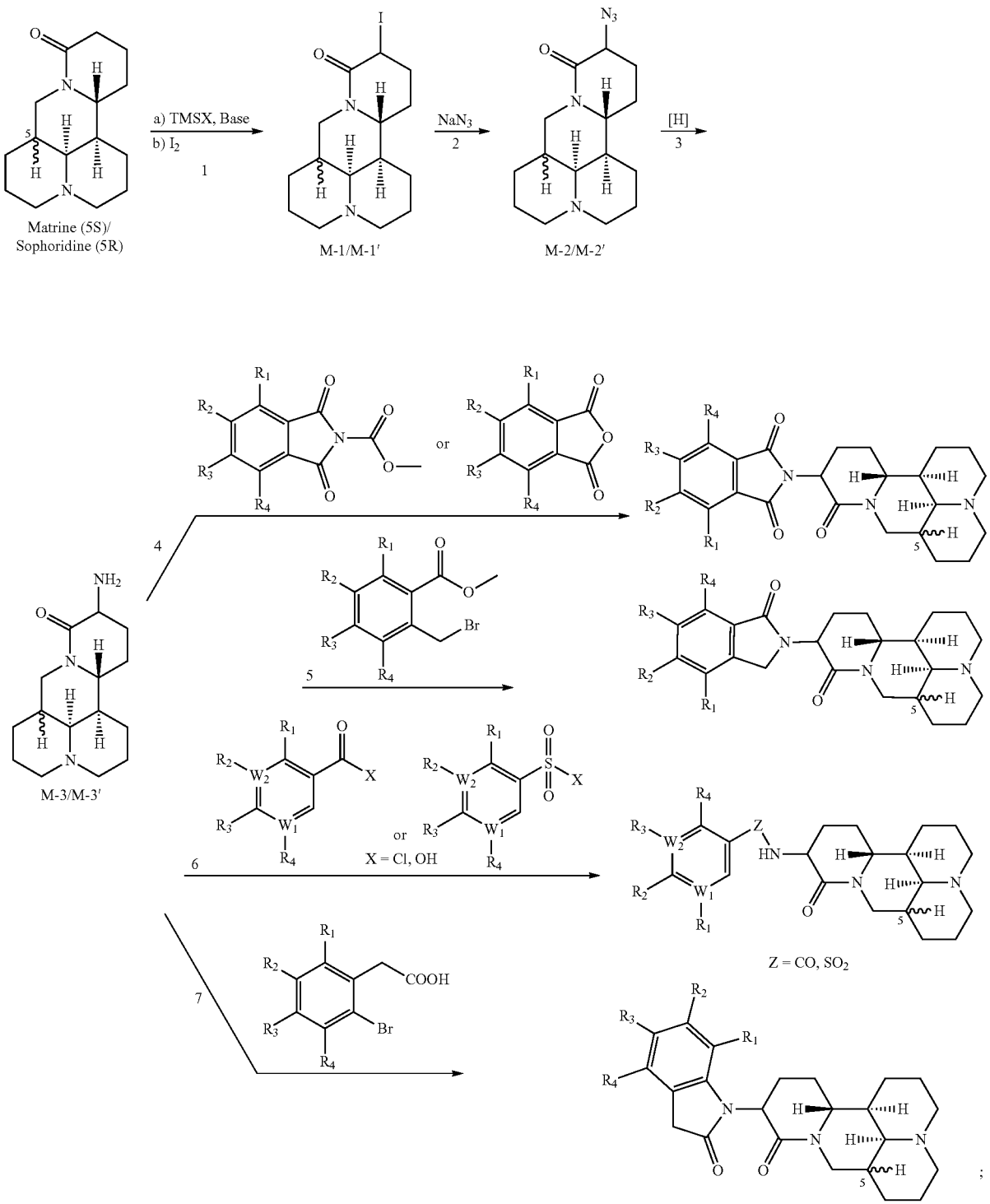

b) The synthesis method for preparing the amino substituted matrine α-ketoamine compounds represented by general formula I-a and I-b.

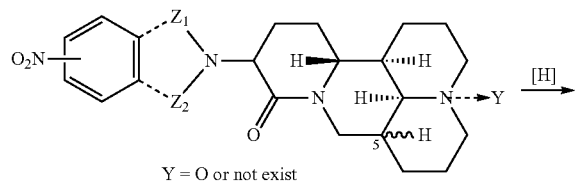

c) The synthesis method for preparing nitrogen oxides represented by general formula I-a and I-b.

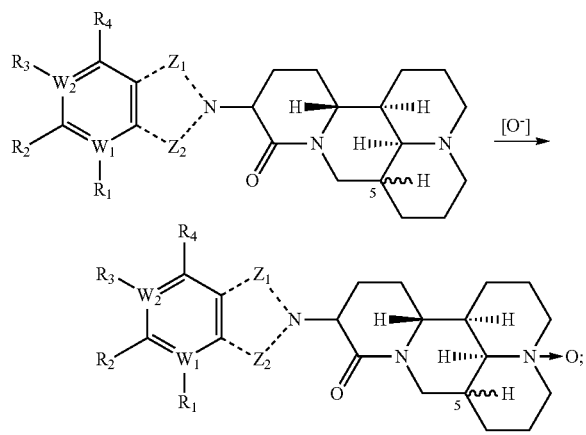

d) The synthesis method for preparing 13,14-dehydromatrine α-ketoamine compounds represented by general formula I-a and I-b.

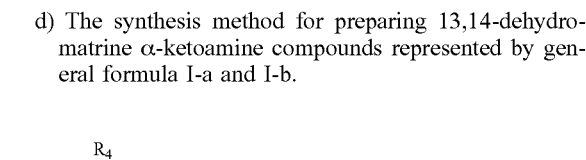

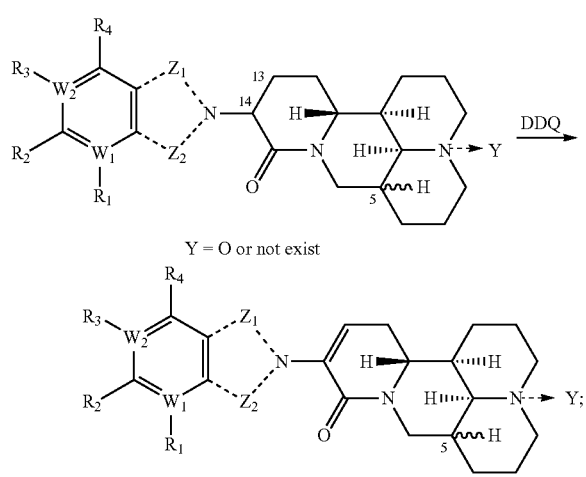

e) The synthesis method for preparing the pharmaceutically acceptable salt of matrine α-ketoamine compounds represented by general formula I-a and I-b.

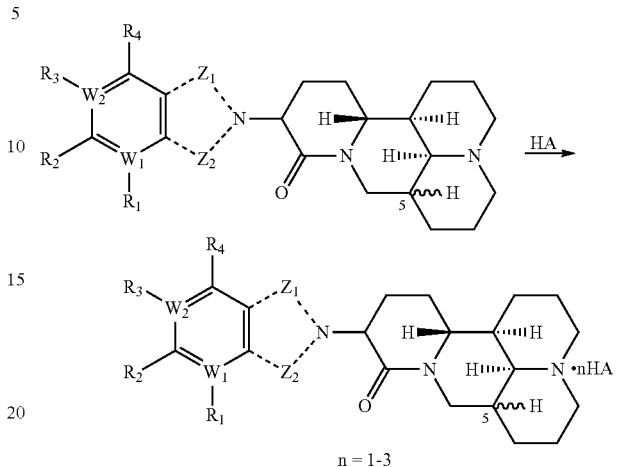

HA refers to hydrochloric acid, sulfuric acid, maleic acid, tartaric acid, methanesulfonic acid, etc.

The synthesis route for preparing the matrine α-ketoamine derivatives represented by general formula I-a, using matrine or sophoridine as raw materials, which can react with halogen at carbonyl alpha-site to afford the corresponding intermediate M-1 or M-1' (step 1), and then can obtain the azide intermediates M-2 or M-2' via the $S_N2$ reaction (step 2), followed by a reduction reaction to form the key intermediates M-3 or M-3' (step 3). Correspondingly, the key intermediates M-3 or M-3' can react with different N-formylmethyl phthalimides or phthalic anhydrides to afford substituted phthalimide matrine or sophoridine compounds respectively (step 4), and can also react with different alkoxyformyl benzyl bromide to afford substituted isoindolin-1-one matrine or sophoridine compounds respectively (step 5), as well as can react with aromatic formic acid or aromatic sulfonic acid to afford the substituted acyl (sulfonyl) matrine or sophoridine compounds respectively (step 6). Moreover, M-3 and M-3' can react with different o-bromophenylacetic acid following by intramolecular cyclization to afford the substituted indolone matrine or sophoridine compounds, respectively.

In step 1, the solvents used include, but are not limited to, tetrahydrofuran, dichloromethane, chloroform, toluene, ether, or a mixed solvent of the above solvents; the organic base used include, but is not limited to triethylamine, diisopropylethylamine, or TMEDA; the trimethylhalosilanes used include, but are not limited to trimethyliodosilane (TMSI), trimethylchlorosilane (TMSCl), etc. The reaction can be performed at the temperature range from −20° C. to room temperature for about 0.5 to 1 hour; after that, $I_2$ or N-iodosuccinimide is added and continue to react for 0.5 to 6 hours. After the reaction is completed, the reaction can be quenched by 10% sodium thiosulfate, and obtain M-1 or M-1' by conventional procedure.

In step 2, the solvents used include, but are not limited to, N, N-dimethylformamide, dimethyl sulfoxide, acetonitrile and water, as well as their mixed solvent that contain $C_1$ to $C_{18}$ carboxylic acid, aryl acid, aralkyl acid, $C_1$~$C_6$ alkyl sulfonic acid or inorganic acid; the azide can be $NaN_3$, and the reaction is performed in the temperature range from 0° C. to 80° C. After the reaction is completed, the intermediate M-2 or M-2' can be obtained by conventional procedure.

In step 3, the reduction system can be $PPh_3$, Pd/C $H_2$ or Pd/C $HCOONH_4$ system; the solvents used include, but are not limited to, $C_1$~$C_6$ alkyl alcohols, N, N-dimethylformamide, dimethyl sulfoxide, acetonitrile, tetrahydrofuran, water or a mixed solvent of the above solvents; the reduction reaction is performed in the temperature range from 0° C. to 100° C.; after the reaction is completed, the key intermediate M-3 or M-3' can be obtained by conventional procedure.

In step 4, using the substituted N-formylmethyl phthalimide or phthalic anhydride as the diformylation reagents; and the solvents used include, but are not limited to, N, N-dimethylformamide, dimethyl sulfoxide, acetonitrile, dichloromethane, tetrahydrofuran or a mixed solvent of the above solvents; the bases used but are not limited to triethylamine, diisopropylethylamine, TMEDA; the reaction is performed in the temperature range from 0° C. to 150° C.; the reaction time is about 1 to 24 hours; after the reaction is completed, the target products I-a and/or I-b can be obtained by conventional procedure.

In step 5, using the substituted alkoxyformyl benzyl bromide as the reaction reagents; and the solvents used include, but are not limited to, N, N-dimethylformamide, dimethyl sulfoxide, acetonitrile, dichloromethane, tetrahydrofuran or a mixture of the above solvents; the bases used but are not limited to triethylamine, diisopropylethylamine, N, N, N, N-tetramethylethylenediamine; the substitution reaction is performed in the temperature range from 0° C. to 150° C.; the reaction time is about 1 to 24 hours; after the reaction is completed, the target products I-a and/or I-b can be obtained by conventional procedure.

In step 6, using the substituted arylformyl chloride or arylsulfonic chloride us the acylating reaction reagents; the solvents used include, but are not limited to, N, N-dimethylformamide, dimethyl sulfoxide, acetonitrile, dichloromethane, tetrahydrofuran, or a mixed solvent of the above solvents; the bases used but are not limited to triethylamine, diisopropylethylamine, N, N, N, N-tetramethylethylenediamine; the substitution reaction temperature is from 0° C. to 150° C.; t the substitution reaction is performed in the temperature range from 0° C. to 150° C.; the reaction time is about 1 to 24 hours; after the reaction is completed, the target products I-a can be obtained by conventional procedure.

In step 7, the intramolecular cyclization mechanism is a Ullman coupling reaction, namely, the o-bromophenylacetic matrines can form the target product of I-a via the intramolecular cyclization in the presence of copper reagents such as CuI, CuBr, and ligands such as amino acids, o-phenylenediamine and sugar amines, and inorganic bases such as sodium carbonate, potassium carbonate or cesium carbonate; the solvents used include, but are not limited to, N, N-dimethylformamide, dimethylsulfoxide, acetonitrile, dichloromethane, tetrahydrofuran, or a mixed solvent of the above solvents.

The synthesis of amino substituents matrine α-ketoamine compounds having a structure of formulas I-a and I-b can be obtained by the reduction of the corresponding nitro-substituted compounds. In the Pd/C [H] reduction system, the solvents used include, but are not limited to, $C_1$~$C_6$ alkyl alcohols, N, N-dimethylformamide, dimethyl sulfoxide, acetonitrile, tetrahydrofuran, water, or t a mixed solvent of the above solvents; the reduction system is Pd/C—$H_2$ or Pd/C—$HCOONH_4$ or $NaBH_4$ or $KBH_4$ or $LiBH_4$; the reaction temperature range from 0° C. to 100° C.; the reaction time is about 1 to 24 hours; after the reaction is complete, the desired compound can be obtained by conventional procedure.

The synthesis of matrine α-ketoamine nitrogen oxides having a structure of formulas I-a and I-b can be obtained by the peroxidation of the corresponding matrine α-ketoamine compounds. In the peroxidation reaction system, the solvents used include, but are not limited to, N, N-dimethylformamide, dimethyl sulfoxide, acetonitrile, methylene chloride, water, tetrahydrofuran or a mixed solvent of the above solvents; the oxidizing agent can be hydrogen peroxide ($H_2O_2$), m-CPBA; the reaction temperature range from 0° C. to 150° C.; the reaction time is about 1 to 24 hours; after the reaction is complete, the desired compound can be obtained by conventional procedure.

The synthesis of 13,14-dehydromatrine α-ketoamine compounds having a structure of formulas I-a and I-b can be obtained by the DDQ dehydrogenation of the corresponding matrine α-ketoamine compounds, respectively.

The derivatives of the formula I-a and/or I-b can combine with HA to produce the corresponding pharmaceutically acceptable salts. HA refers to hydrochloric acid, hydrobromic acid, sulfuric acid, phosphoric acid, acetic acid, citric acid, oxalic acid, malonic acid, salicylic acid, malic acid, fumaric acid, succinic acid, mandelic acid, ascorbic acid, maleic acid, tartaric acid, benzenesulfonic acid, methanesulfonic acid or isethionate.

According to the methods of the present invention, the matrine α-ketoamine compounds can be obtained through the synthetic routes of a), b), c), d) and e). The reaction process is usually monitored by TLC and LC-MS, after the reaction is completed, extracting with a solvent such as methyl tert-butyl ether, ethyl acetate or dichloromethane, washing with saturated sodium bicarbonate, water and saturated brine in order, drying over anhydrous sodium sulfate or magnesium sulfate, and removing the solvent under reduced pressure at low temperature. The key intermediate and final products were confirmed by NMR and mass spectrometry.

According to the third object of the present invention, the compounds having a structure of general formula (I) in the present invention, the pharmaceutically acceptable salt, the solvate, the polymorph, the stereoisomer, the isotopic compound or the metabolite thereof, that can be used to include, but are not limited to the preparation of drugs for a disease, disorder, illness or condition caused by the overexpression of TNF-α and normal cells ferroptosis, and can be used as TNF-α inhibitor and/or immunomodulators for the treatment of diseases related to TNF-α overexpression and/or the abnormal immune function of the NK cells, such as autoimmune diseases, neurodegenerative diseases, hematological tumors, solid tumors, myelofibrosis and acute/chronic graft-versus-host disease. The autoimmune diseases include rheumatoid arthritis, inflammatory bowel disease, diabetes, psoriasis, mandatory spondylitis, leprosy nodular erythema, lupus erythematosus, and other infectious diseases such as HBV, HCV, HIV; the neurodegenerative diseases include Alzheimer's disease, dementia, Parkinson's disease, multiple sclerosis, Huntington's disease, amyotrophic lateral sclerosis (ALS), different types of spinocerebellar ataxia (SCA), pick's disease; the blood tumor refers to myelodysplastic syndrome, chronic lymphoblastic leukemia, multiple myeloma, mantle cell lymphoma, non-Hodgkin's lymphoma, chronic myelomonocytic leukemia, T-cell lymphoma, erythroid lymphoma, monocyte and monocyte leukemia, myeloid leukemia, myelofibrosis, Burkitt's lymphoma, Hodgkin's lymphoma, large cell lymphoma, diffuse large B cell lymphoma; the solid tumor refers to liver cancer, kidney cancer, gastric cancer, colon cancer, ovarian cancer, pancreatic cancer, prostate cancer, breast cancer, melanoma, papillary and follicular thyroid cancer, glioblastoma, gliosarcoma, malignant glioma, refractory plasmacytoma, ciliary body and chronic melanoma, iris melanoma, recurrent interocular melanoma and extraocular extended melanoma, brain tumor, meningioma, spinal cord tumor, thyroid cancer, non-small cell lung cancer, skin cancer, stellate cell tumor.

Beneficial Effect

The present invention developed a new series of matrine α-ketoamine compounds, which showed significant inhibitory effect on TNF-α overexpression and activate the immune killing function of the NK cells comparing with the known matrines, thereby could be used as TNF-α inhibitor and/or immunomodulator for treating disease.

EXAMPLES

Figure 1:
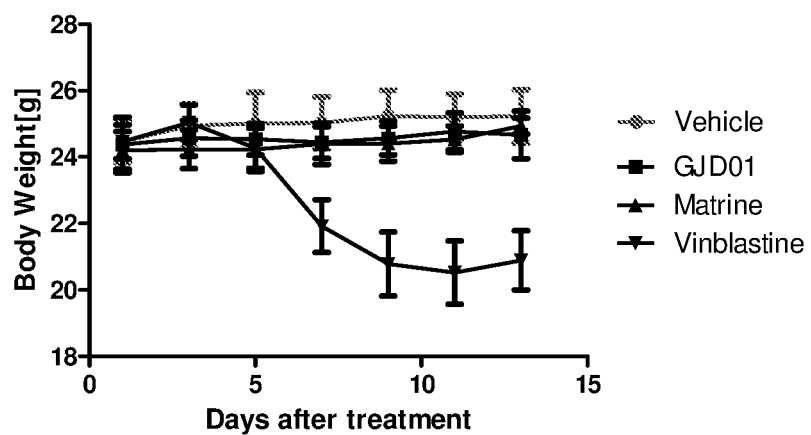
FIG. 1 is the weight change curve of nude mice model of A549 xenograft tumor during intervention.

The present invention will now be further elucidated by way of a description of a preferred exemplary embodiment of the invention but is not limited thereto. Each preferred condition aforementioned can be combined randomly without departing from the common knowledge in the art thereby forming various preferred embodiments of the present invention.

In the following embodiments, 1H-NMR was measured with a Varian Mercury AMX300 instrument. MS was measured with VG ZAB-HS or VG-7070 and Esquire 3000Plus-01005. All reaction solvents are redistilled before use, and the anhydrous solvents are obtained in accordance with standard drying methods. Unless otherwise indicated, all reactions were carried out under the protection of argon and monitored by TLC and following the conventional workup and pre-drying treatment by saturated saline and anhydrous sodium sulfate. Products were purified by column chromatography on silica gel (200-300 mesh) unless otherwise stated.

Example 1. Synthesis of Compound M-3

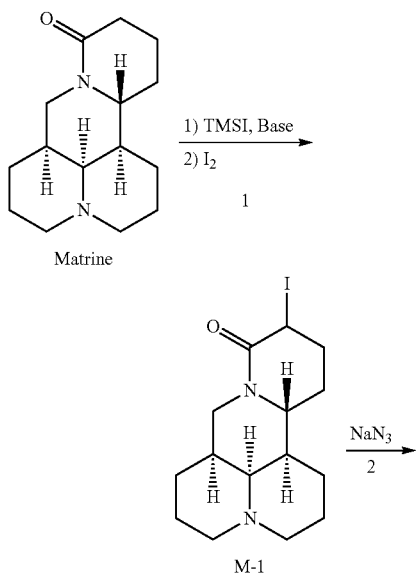

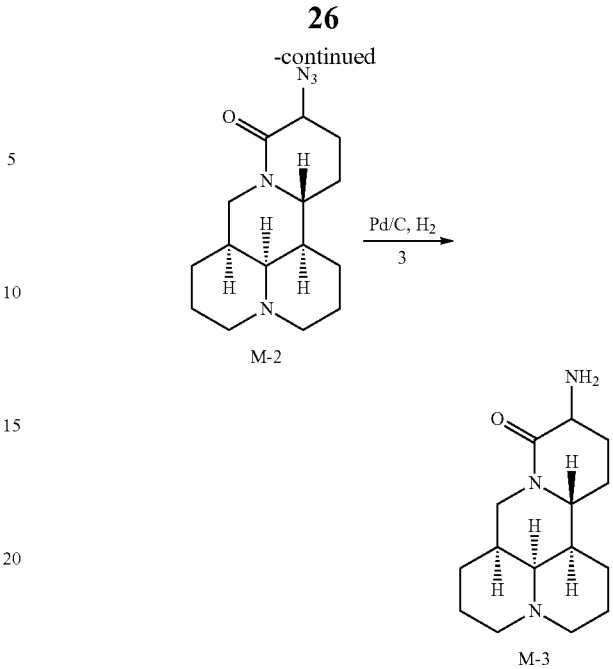

Step 1: Preparation of Intermediate M-1

To a stirred solution of matrine (4.96 g, 20 mmol) and triethylamine (4.04 g, 40 mmol) in dichloromethane (200 mL) was slowly added trimethylchlorosilane (2.60 g, 24 mmol) under an ice bath, after 1 h, iodine (6.10 g, 24 mmol) was added, and the reaction was continued for the further 3 to 5 hours at this condition. After the reaction was completed, quenching with 200 ml of 10% sodium thiosulfate solution, followed by extraction with dichloromethane (200 mL×3). The combined organic phases were sequentially washed with saturated sodium bicarbonate, saturated brine, dried over anhydrous sodium sulfate, and filtered. The resulting filtrate was evaporated under reduced pressure and purified by silica gel column chromatography ($V_{chloroform}$:$V_{methanol}$=30:1 to 10:1) to obtain M-1 (6.88 g, yield 92%). MS-ESI [M+H]$^+$ 375.1 (375.1).

Step 2: Preparation of Intermediate M-2

An aqueous solution (6.7 mL) of sodium azide (1.62 g, 25 mmol) was added dropwise to a stirred mixed solution (DMF 38 mL and acetic acid 0.67 mL) of M-1 (3.74 g, 10 mmol) under ice bath. After the reaction was completed (monitored by TLC), ice-water (100 mL) was added, followed by extraction with dichloromethane (30 mL×2). The organic phase was sequentially washed with saturated sodium bicarbonate, saturated brine, dried over anhydrous sodium sulfate, and filtered. The resulting filtrate was evaporated under reduced pressure and purified by silica gel column chromatography. ($V_{chloroform}$:$V_{methanol}$=60:1 to 20:1) to obtain M-2 (1.88 g, yield 65%). HRMS-ESI: m/z calcd for $C_{15}H_{23}N_5O$: 289.1903, found [M+H]$^+$ 290.1981; 1H NMR (400 MHz, CDCl$_3$) δ 4.28 (dd, J=12.9, 4.4 Hz, 1H), 3.86 (dd, J=11.1, 5.3 Hz, 1H), 3.76 (td, J=10.9, 5.4 Hz, 1H), 3.07 (t, J=12.8 Hz, 1H), 2.81-2.69 (m, 2H), 2.17-2.10 (m, 1H), 2.05-1.97 (m, 2H), 1.96-1.78 (m, 3H), 1.73-1.47 (m, 6H), 1.43-1.34 (m, 5H).

Step 3: Preparation of Intermediate M-3

To a stirred solution of M-2 (1.44 g, 5 mmol) in methanol (25 mL) was added 10% Pd/C, and then the mixture was reacted under H$_2$ (50 Psi) atmosphere overnight. After the reaction was completed, filtered, and the filtrate was evaporated under reduced pressure to give M-3 (1.33 g). HRMS- ESI: m/z calcd for $C_{15}H_{25}N_3O$: 263.1998, found [M+H]$^+$ 264.2072; 1H NMR (400 MHZ, CD$_3$OD) δ 4.29 (dd, J=12.9, 4.4 Hz, 1H), 3.89-3.76 (m, 1H), 3.46-3.35 (m, 1H), 3.15-3.05 (m, 1H), 2.90-2.83 (m, 2H), 2.37-1.97 (m, 6H), 1.71-1.60 (m, 6H), 1.58-1.37 (m, 5H).

Example 2 Synthesis of Compound M-3'

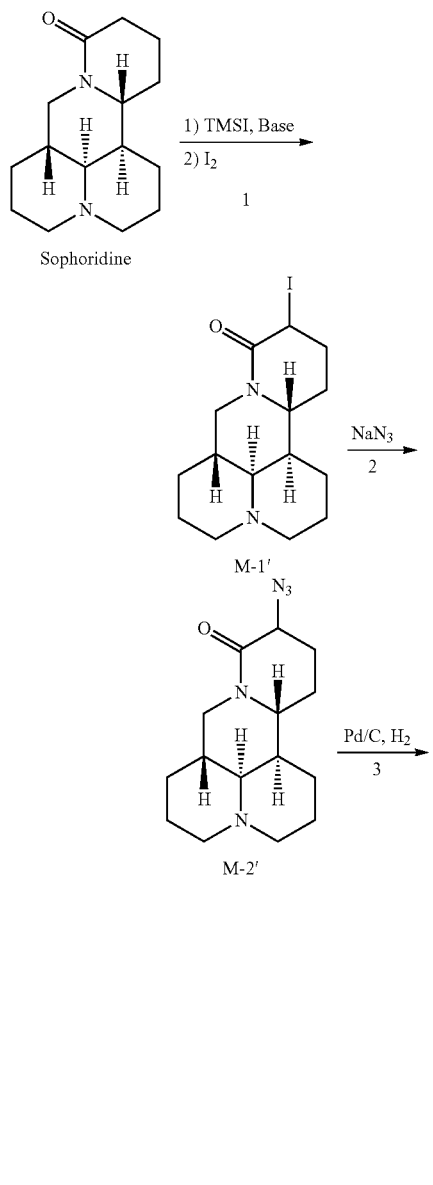

Step 1: preparation of intermediate M-1'

To a stirred solution of sophoridine (4.96 g, 20 mmol) and triethylamine (4.04 g, 40 mmol) in dichloromethane (400 mL) was slowly added trimethyliodosilane (2.00 g, 10 mmol) under an ice bath, after 1 h, iodine (6.10 g, 24 mmol) was added, and the reaction was continued for the further 3 to 5 hours at this condition. After the reaction was completed, quenching with 200 ml of 10% sodium thiosulfate solution, followed by extraction with dichloromethane (200 mL×3). The combined organic phases were sequentially washed with saturated sodium bicarbonate, saturated brine, dried over anhydrous sodium sulfate, and filtered. The resulting filtrate was evaporated under reduced pressure and purified by silica gel column chromatography (V$_{chloroform}$:V$_{methanol}$=30:1 to 10:1) to obtain M-1' (6.72 g, yield 90%). MS-ESI [M+H]$^+$ 375.1 (375.1).

Step 2: Preparation of Intermediate M-2'

An aqueous solution (6.7 mL) of sodium azide (1.62 g, 25 mmol) was added dropwise to a stirred mixed solution (DMF 38 mL and acetic acid 0.67 mL) of M-1 (3.74 g, 10 mmol) under ice bath. After the reaction was completed (monitored by TLC), ice-water (100 mL) was added, followed by extraction with dichloromethane (30 mL×2). The organic phase was sequentially washed with saturated sodium bicarbonate, saturated brine, dried over anhydrous sodium sulfate, and filtered. The resulting filtrate was evaporated under reduced pressure and purified by silica gel column chromatography (V$_{chloroform}$:V$_{methanol}$=30:1 to 10:1) to obtain M-2' (2.02 g, yield 70%). HRMS-ESI: m/z calcd for $C_{15}H_{23}N_5O$: 289.1903, found [M+H]$^+$ 290.1981. $^1$H NMR (300 MHz, CDCl$_3$) δ 3.87-3.66 (m, 2H), 3.51-3.43 (m, 1H), 3.31-3.15 (m, 1H), 2.96-2.87 (m, 2H), 2.89-2.80 (m, 1H), 2.63-2.05 (m, 4H), 2.01-1.65 (m, 4H), 1.62-1.47 (m, 6H), 1.35-1.03 (m, 2H).

Step 3: Preparation of Intermediate M-3'

To a stirred solution of M-2' (1.44 g, 5 mmol) in methanol (25 mL) was added 10% Pd/C, and then the mixture was reacted under H$_2$ (50 Psi) atmosphere for overnight. After the reaction was completed, filtered, and the filtrate was evaporated under reduced pressure to give M-3' (1.33 g, quantitative). HRMS-ESI: m/z calcd for $C_{15}H_{25}N_3O$: 263.1998, found [M+H]$^+$ 264.2072; $^1$H NMR (400 MHZ, CD$_3$OD) δ 3.92-3.79 (m, 2H), 3.58-3.45 (m, 1H), 3.30-3.12 (m, 1H), 2.96-2.89 (m, 2H), 2.89-2.80 (m, 1H), 2.63-2.05 (m, 4H), 2.01-1.65 (m, 4H), 1.62-1.48 (m, 6H), 1.35-1.04 (m, 2H).

Example 3 Synthesis of Compound GJD-1

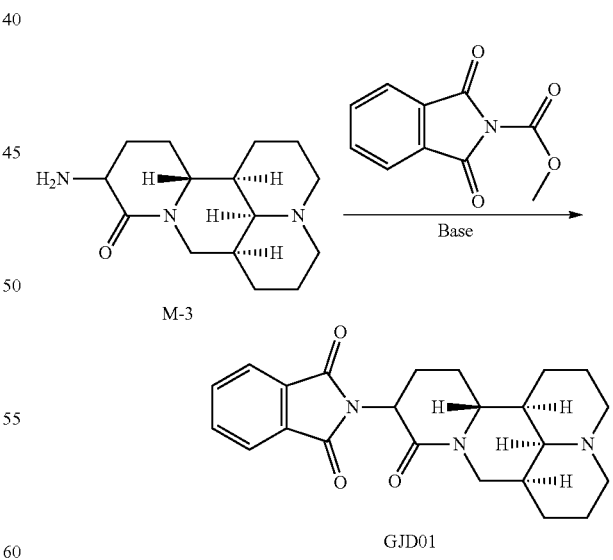

To a stirred solution of M-3 (53 mg, 0.2 mmol) and triethylamine (30 mg, 0.3 mmol) in tetrahydrofuran (1 mL) was added N-formylmethyl-substituted phthalimide (45 mg, 0.22 mmol), and the reaction was heated to 60° C. for overnight. After the reaction was completed, filtered, and the filtrate was evaporated and purified by silica gel column chromatography ($V_{chloroform}:V_{methanol}$=40:1 to 20:1) to give the compound GJD01 (68 mg, yield 76%) of example 3. HRMS-ESI: m/z calcd for $C_{23}H_{27}N_3O_3$: 393.2052, found [M+H]$^+$394.2126; 1H NMR (300 MHZ, CDCl$_3$) δ 7.90-7.74 (m, 2H), 7.73-7.59 (m, 2H), 4.70 (dd, J=12.9, 5.4 Hz, 1H), 4.34 (dd, J=13.0, 4.4 Hz, 1H), 3.98 (td, J=10.6, 5.4 Hz, 1H), 3.22 (t, J=12.9 Hz, 1H), 2.92-2.73 (m, 2H), 2.60-2.46 (m, 1H), 2.38-2.30 (m, 1H), 2.07-1.88 (m, 5H), 1.77-1.38 (m, 10H). $^{13}$C NMR (101 MHZ, CDCl$_3$) δ 168.0 (2C), 165.7, 133.9 (2C), 132.2 (2C), 123.4 (2C), 63.2, 57.2, 57.1, 53.3, 50.3, 43.9, 41.7, 34.9, 27.7, 27.1, 26.2, 24.2, 21.1, 20.7.

Example 2 to 21 were performed according to the operation of example 3, wherein the synthesis of different N-methyl formate substituted phthalimides that used for reacting with M-3 could follow the reference methods (*Bioorg Med Chem Lett.* 2017, 27, 4075, U.S. Pat. No. 6,335,349B1, U.S. Pat. No. 9,821,068B2). Examples of results obtained are as follows:

| Example | yields | compound | (HR)MS-ESI and $^1$H NMR |
|---|---|---|---|
| 4 | 93% | GJD03 | HRMS-ESI: m/z calcd for $C_{23}H_{26}FN_3O_3$: 411.1958, found [M+H]$^+$ 412.2035; $^1$H NMR (300 MHz, CDCl$_3$) δ 7.80-7.49 (m, 3H), 4.68 (dd, J = 12.9, 5.4 Hz, 1H), 4.33-3.95 (m, 2H), 3.21 (t, J = 13.0 Hz, 1H), 2.92-2.73 (m, 2H), 2.55-2.42 (m, 1H), 2.35-1.33 (m, 16H). |
| 5 | 82% | GJD04 | HRMS-ESI: m/z calcd for $C_{23}H_{26}ClN_3O_3$: 427.1663, found [M+H]$^+$ 428.1742; $^1$H NMR (300 MHz, CDCl$_3$) δ 7.97-7.71 (m, 3H), 4.71 (dd, J = 12.9, 5.4 Hz, 1H), 4.35 (dd, J = 13.0, 4.5 Hz, 1H), 4.06-3.95 (m, 1H), 3.22 (t, J = 13.0 Hz, 1H), 2.91-2.74 (m, 2H), 2.54-2.43 (m, 1H), 2.36-1.32 (m, 16H). |
| 6 | 81% | GJD05 | HRMS-ESI: m/z calcd for $C_{23}H_{26}N_4O_5$: 438.1903, found [M+H]$^+$ 439.1782; $^1$H NMR (300 MHz, CDCl$_3$) δ 8.15-8.09 (m, 2H), 7.92-7.86 (m, 1H), 4.81 (dd, J = 12.9, 5.4 Hz, 1H), 4.33-4.10 (m, 2H), 3.21 (t, J = 12.9 Hz, 1H), 2.92-2.75 (m, 2H), 2.56-2.43 (m, 1H), 2.35-1.88 (m, 6H), 1.77-1.38 (m, 10H). |
| 7 | 87% | GJD06 | HRMS-ESI: m/z calcd for $C_{23}H_{26}N_4O_5$: 438.1903, found [M+H]$^+$ 439.1782; $^1$H NMR (300 MHz, CDCl$_3$) δ 8.16-7.74 (m, 3H), 4.75 (dd, J = 12.9, 5.4 Hz, 1H), 4.33-4.06 (m, 2H), 3.22 (t, J = 12.9 Hz, 1H), 2.91-2.73 (m, 2H), 2.56-2.42 (m, 1H), 2.34-1.85 (m, 6H), 1.78-1.36 (m, 10H). |
| 8 | 75% | GJD07 | HRMS-ESI: m/z calcd for $C_{24}H_{26}F_3N_3O_3$: 461.1926, found [M+H]$^+$ 462.2002; $^1$H NMR (300 MHz, CDCl$_3$) δ 8.06-7.78 (m, 3H), 4.72 (dd, J = 12.9, 5.3 Hz, 1H), 4.35-3.96 (m, 2H), 3.20 (t, J = 12.9 Hz, 1H), 2.93-2.73 (m, 2H), 2.56-2.41 (m, 1H), 2.36-1.86 (m, 6H), 1.77-1.34 (m, 10H). |
| 9 | 69% | GJD08 | HRMS-ESI: m/z calcd for $C_{24}H_{29}N_3O_3$: 407.2209, found [M+H]$^+$ 408.2280; $^1$H NMR (300 MHz, CDCl$_3$) δ 7.98-7.45 (m, 3H), 4.68 (dd, J = 12.9, 5.4 Hz, 1H), 4.33-3.80 (m, 2H), 3.21 (t, J = 12.9 Hz, 1H), 2.91-2.74 (m, 2H), 2.65-2.53 (m, 1H), 2.35-1.87 (m, 9H), 1.77-1.33 (m, 10H). |
| 10 | 90% | GJD09 | HRMS-ESI: m/z calcd for $C_{24}H_{29}N_3O_4$: 423.2158, found [M+H]$^+$ 424.2230; $^1$H NMR (300 MHz, CDCl$_3$) δ 8.07-7.94 (m, 1H), 7.73-7.46 (m, 2H), 4.69 (dd, J = 12.9, 5.4 Hz, 1H), 4.34-3.83 (m, 5H), 3.21 (t, J = 12.9 Hz, 1H), 2.93-2.71 (m, 2H), 2.65-2.52 (m, 1H), 2.37-1.88 (m, 6H), 1.76-1.34 (m, 10H). |
| 11 | 61% | GJD10 | HRMS-ESI: m/z calcd for $C_{23}H_{27}N_3O_4$: 417.2052, found [M+H]$^+$ 418.2130; $^1$H NMR (300 MHz, CDCl$_3$) δ 7.90-7.49 (m, 3H), 4.72-4.68 (m, 1H), 4.34-3.92 (m, 2H), 3.23 (t, J = 12.9 Hz, 1H), 2.91-2.73 (m, 2H), 2.63-2.44 (m, 1H), 2.38-2.31 (m, 1H), 2.07-1.89 (m, 5H), 1.78-1.36 (m, 10H). |
| 12 | 92% | GJD11 | HRMS-ESI: m/z calcd for $C_{25}H_{27}N_3O_3$: 409.2002, found [M+H]$^+$ 410.2080; $^1$H NMR (300 MHz, CDCl$_3$) δ 7.65 (t, J = 7.8 Hz 1H), 7.20-7.15 (m, 2H), 6.51 (t, J = 5.8 Hz, 1H), 4.71-4.66 (m, 1H), 4.34-3.94 (m, 2H), 3.22 (t, J = 12.9 Hz, 1H), 2.91-2.73 (m, 2H), 2.63-2.44 (m, 1H), 2.38-2.31 (m, 1H), 2.07-1.86 (m, 5H), 1.78-1.37 (m, 10H), 1.01-0.83 (m, 6H). |
| 13 | 93% | GJD12 | MS-ESI [M+H]$^+$ 451.2 (451.2); $^1$H NMR (300 MHz, CDCl$_3$) δ 9.51 (brs, 1H), 8.76 (d, J = 8.5 Hz, 1H), 7.70-7.62 (m, 1H), 7.51 (d, J = 7.4 Hz, 1H), 4.68 (dd, J = 13.0, 5.4 Hz, 1H), 4.36 (dd, J = 13.0, 4.5 Hz, 1H), 4.02-3.95 (m, 1H), 3.24 (t, J = 13.0 Hz, 1H), 2.90-2.74 (m, 2H), 2.52-2.42 (m, 1H), 2.36-2.30 (m, 1H), 2.26 (s, 3H), 2.09-1.36 (m, 15H). |
| 14 | 86% | GJD13 | HRMS-ESI: m/z calcd for $C_{25}H_{30}N_4O_4$: 450.2267, found [M+H]$^+$ 451.2347; $^1$H NMR (300 MHz, CDCl$_3$) δ 9.91-7.52 (m, 4H), 4.68 (dd, J = 13.0, 5.4 Hz, 1H), 4.34 (dd, J = 12.9, 4.5 Hz, 1H), 4.02-3.95 (m, 1H), 3.23 (t, J = 12.9 Hz, 1H), 2.98-2.73 (m, 5H), 2.55-1.34 (m, 17H). |
| 15 | 71% | GJD14 | HRMS-ESI: m/z calcd for $C_{24}H_{30}N_4O_5S$: 486.1937, found [M+H]$^+$ 487.2017; $^1$H NMR (300 MHz, CDCl$_3$) δ 8.45-8.26 (m, 2H), 8.03-7.92 (m, 1H), 4.83 (dd, J = 12.9, 5.4 Hz, 1H), 4.37-4.12 (m, 2H), 3.24 (t, J = 12.9 Hz, 1H), 2.94-2.77 (m, 2H), 2.58-1.38 (m, 17H). |

| Example | yields | compound | (HR)MS-ESI and $^1$H NMR |
|---|---|---|---|
| 16 | 82% | GJD15 | HRMS-ESI: m/z calcd for $C_{22}H_{26}N_4O_3$: 394.2005, found [M+H]$^+$ 395.2080; MS-ESI [M+H]$^+$ 395.2 (395.2); $^1$H NMR (300 MHz, CDCl$_3$) δ 9.16-8.06 (m, 3H), 4.87-4.72 (m, 1H), 4.38-4.10 (m, 2H), 3.22 (t, J = 12.9 Hz, 1H), 2.94-2.77 (m, 2H), 2.58-1.37 (m, 17H). |
| 17 | 64% | GJD16 | HRMS-ESI: m/z calcd for $C_{24}H_{29}N_3O_4$: 423.2158, found [M+H]$^+$ 424.2230. |
| 18 | 89% | GJD17 | MS-ESI [M+H]$^+$ 527.3 (527.3); $^1$H NMR (300 MHz, CDCl$_3$) δ8.34 (s, 1H), 7.65-7.18 (m, 7H), 4.76-4.67 (m, 1H), 4.34-3.93 (m, 2H), 3.22 (t, J = 12.9 Hz, 1H), 2.91-2.73 (m, 2H), 2.63-2.44 (m, 1H), 2.38-2.32 (m, 1H), 2.10-1.85 (m, 6H), 1.78-1.36 (m, 10H), 1.24-1.20 (m, 6H), 1.01-0.83 (m, 6H). |
| 19 | 82% | GJD19 | HRMS-ESI: m/z calcd for $C_{25}H_{31}N_3O_5$: 453.2264, found [M+H]$^+$ 454.2240. |
| 20 | 83% | GJD20 | MS-ESI [M+H]$^+$ 412.2 (412.2); $^1$H NMR (300 MHz, CDCl$_3$) δ 7.81-7.37 (m, 3H), 4.75-4.68 (m, 1H), 4.35-3.97 (m, 2H), 3.22 (t, J = 13.0 Hz, 1H), 2.92-2.73 (m, 2H), 2.55-2.42 (m, 1H), 2.36-1.32 (m, 16H). |
| 21 | 81% | GJD21 | MS-ESI [M+H]$^+$ 410.2 (410.2); $^1$H NMR (300 MHz, CDCl$_3$) δ 7.91-7.38 (m, 3H), 4.72-4.65 (m, 1H), 4.34-3.93 (m, 2H), 3.23 (t, J = 12.9 Hz, 1H), 2.91-2.72 (m, 2H), 2.63-2.44 (m, 1H), 2.38-2.30 (m, 1H), 2.07-1.86 (m, 5H), 1.78-1.33 (m, 10H). |

Example 22 to 23 were performed according to the operation of example 3 also, wherein the raw material of M-3 that used for substrates expanding was changed to M-3'. Examples of results obtained are as follows:

| Example | yields | compound | (HR)MS-ESI and $^1$H NMR |
|---|---|---|---|
| 22 | 83% | GJD28 | HRMS-ESI: m/z calcd for $C_{23}H_{27}N_3O_3$: 393.2052, found [M+H]$^+$ 394.2126; $^1$H NMR (300 MHz, CDCl$_3$) δ 7.91-7.58 (m, 4H), 4.72-4.63 (m, 1H), 3.80-3.61 (m, 1H), 3.58-3.45 (m, 1H), 3.30-3.12 (m, 1H), 2.96-2.89 (m, 2H), 2.89-2.80 (m, 1H), 2.63-2.05 (m, 4H), 2.01-1.65 (m, 4H), 1.62-1.48 (m, 6H), 1.35-1.04 (m, 2H). |
| 23 | 72% | GJD29 | HRMS-ESI: m/z calcd for $C_{24}H_{29}N_3O_3$: 407.2209, found [M+H]$^+$ 408.2280; $^1$H NMR (300 MHz, CDCl$_3$) δ 7.98-7.45 (m, 3H), 4.72-4.63 (m, 1H), 3.80-3.61 (m, 1H), 3.58-3.45 (m, 1H), 3.30-3.12 (m, 1H), 2.93-2.79 (m, 3H), 2.63-1.45 (m, 17H), 1.36-1.03 (m, 2H). |

Example 24 Synthesis of Compound GJD30

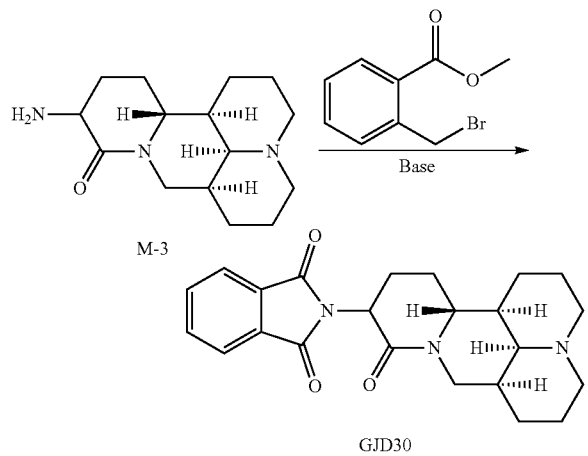

M-3 (53 mg, 0.2 mmol), 2-bromomethyl-benzoic acid methyl ester (46 mg, 0.2 mmol) and KHCO$_3$ (40 mg, 0.4 mmol) were added to a CH$_3$CN (1 mL) solution, and the resulting reaction mixture was performed at 95° C. for overnight. After the reaction was completed, filtered, and the filtrate was evaporated and purified by silica gel column chromatography (V$_{chloroform}$:V$_{methanol}$=80:1 to 40:1) to give the compound GJD30 of example 24 (67 mg, yield 89%). HRMS-ESI: m/z calcd for $C_{23}H_{29}N_3O_2$: 379.2260, found [M+H]$^+$380.2335.

Example 25 to 36 were performed according to the operation of example 24, wherein the synthesis of different 2-bromomethyl-methylbenzoates that used for reacting with M-3 could follow the reference methods (S. Huet. et al. *Bioorg Med Chem Lett.* 2017, 27, 4075, US 2003/0028028, C. Contino-Pépin. et al. *Bioorg. Med. Chem. Lett.* 2009, 19, 878, AL Ruchelman. et al. *Bioorg. Med. Chem. Lett.* 2013, 23, 360.). Examples of results obtained are as follows:

| Example | yields | compound | (HR)MS-ESI and $^1$H NMR |
|---|---|---|---|
| 26 | 72% | GJD31 | HRMS-ESI: m/z calcd for $C_{23}H_{28}N_4O_4$: 424.2111, found [M+H]$^+$ 425.2188. $^1$H NMR (300 MHz, CDCl$_3$) δ 8.42-7.69 (m, 3H), 4.93-4.35 (m, 4H), 4.02 (td, J = 10.6, 5.4 Hz, 1H), 3.22 (t, J = 12.9 Hz, 1H), 2.92-2.75 (m, 2H), 2.33-2.21 (m, 2H), 2.08-1.87 (m, 5H), 1.79-1.38 (m, 10H). |
| 27 | 68% | GJD 32 | HRMS-ESI: m/z calcd for $C_{24}H_{28}N_4O_2$: 404.2212, found [M+H]$^+$ 405.2290. |
| 28 | 76% | GJD 33 | HRMS-ESI: m/z calcd for $C_{25}H_{32}N_4O_3$: 436.2474, found [M+H]$^+$ 437.2550; $^1$H NMR (300 MHz, CDCl$_3$) δ 9.84 (brs, 1H), 7.81 (d, J = 7.0 Hz, 1H), 7.60-7.45 (m, 2H), 4.94-4.64 (m, 1H), 4.47-4.22 (m, 3H), 4.07-3.84 (m, 1H), 3.20 (t, J = 12.9 Hz, 1H), 2.89-2.77 (m, 2H), 2.33-2.21 (m, 2H), 2.12-1.85 (m, 8H), 1.77-1.37 (m, 10H). |
| 29 | 81% | GJD 34 | HRMS-ESI: m/z calcd for $C_{30}H_{34}N_4O_3$: 498.2631, found [M+H]$^+$ 499.2705; $^1$H NMR (300 MHz, CDCl$_3$) δ 10.34 (brs, 1H), 7.97 (d, J = 7.2 Hz, 2H), 7.72 (d, J = 8.0 Hz, 1H), 7.55-7.43 (m, 5H), 5.09-4.90 (m, 1H), 4.47-4.22 (m, 3H), 4.07-3.84 (m, 1H), 3.20 (t, J = 12.9 Hz, 1H), 2.89-2.77 (m, 2H), 2.33-1.85 (m, 7H), 1.77-1.38 (m, 10H). |
| 30 | 83% | GJD 36 | HRMS-ESI: m/z calcd for $C_{23}H_{28}FN_3O_2$: 397.2166, found [M+H]$^+$ 398.2240. |
| 31 | 87% | GJD 37 | HRMS-ESI: m/z calcd for $C_{23}H_{29}N_3O_3$: 395.2209, found [M+H]$^+$ 396.2280; $^1$H NMR (300 MHz, DMSO-d$_6$) δ 7.78-7.52 (m, 2H), 6.80-6.66 (m, 1H), 4.92-4.61 (m, 1H), 4.43-4.19 (m, 3H), 4.07-3.85 (m, 1H), 3.23-3.10 (m, 1H), 2.86-2.75 (m, 2H), 2.33-2.21 (m, 2H), 2.08-1.86 (m, 5H), 1.76-1.37 (m, 10H). |
| 32 | 80% | GJD 38 | HRMS-ESI: m/z calcd for $C_{24}H_{31}N_3O_2$: 393.2416, found [M+H]$^+$ 394.2490; $^1$H NMR (300 MHz, CDCl$_3$) δ 7.69 (d, J = 7.4 Hz, 1H), 7.36-7.30 (m, 2H), 4.70-4.34 (m, 4H), 3.98 (td, J = 10.6, 5.4 Hz, 1H), 3.22 (t, J = 12.9 Hz, 1H), 2.92-2.73 (m, 2H), 2.60-2.46 (m, 1H), 2.38-2.30 (m, 4H), 2.07-1.88 (m, 5H), 1.77-1.37 (m, 10H). |
| 33 | 72% | GJD 39 | HRMS-ESI: m/z calcd for $C_{23}H_{28}N_4O_4$: 424.2111, found [M+H]$^+$ 425.2180; $^1$H NMR (300 MHz, CDCl$_3$) δ 8.48-7.91 (m, 3H), 5.09-4.90 (m, 1H), 4.47-4.22 (m, 3H), 4.11-3.87 (m, 1H), 3.22 (t, J = 13.0 Hz, 1H), 2.89-2.78 (m, 2H), 2.33-2.20 (m, 2H), 2.12-1.86 (m, 5H), 1.79-1.39 (m, 10H). |
| 34 | 77% | GJD 42 | HRMS-ESI: m/z calcd for $C_{23}H_{29}N_3O_2$: 379.2260, found [M+H]$^+$ 380.2335. |
| 35 | 74% | GJD 44 | HRMS-ESI: m/z calcd for $C_{24}H_{31}N_3O_2$: 393.2416, found [M+H]$^+$ 394.2492. |
| 36 | 75% | GJD 45 | HRMS-ESI: m/z calcd for $C_{23}H_{28}N_4O_4$: 424.2111, found [M+H]$^+$ 425.2185. $^1$H NMR (300 MHz, CDCl$_3$) δ 8.42-7.64 (m, 3H), 4.82-4.43 (m, 3H), 3.80-3.61 (m, 1H), 3.58-3.45 (m, 1H), 3.30-3.12 (m, 1H), 2.93-2.79 (m, 3H), 2.63-1.42 (m, 14H), 1.36-1.01 (m, 2H). |

Example 37. Synthesis of Compound GJD22

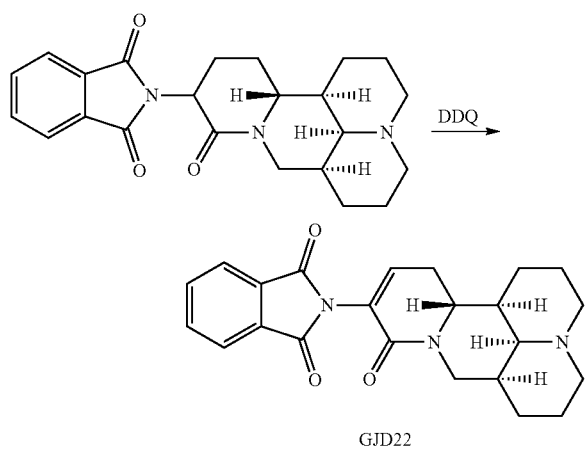

GJD01 (79 mg, 0.2 mmol) and DDQ (46 mg, 0.2 mmol) were added to a chlorobenzene solution (2 mL) under nitrogen atmosphere, and the reaction was performed at 120° C. for 24 h. After the reaction was completed (monitored by TLC), the reaction was cooled to room temperature, and then sodium sulfite (63 mg, 0.5 mmol) was added and continued to react for 1 hour, filtered, the filtrate was evaporated and purified by a basic alumina column chromatography (V$_{chloroform}$:V$_{methanol}$=40:1~20:1) to give the compound GJD22 (32 mg, yield 40%) of example 37. HRMS-ESI: m/z calcd for $C_{23}H_{25}N_3O_3$: 391.1896, found [M+H]$^+$392.1977. $^1$H NMR (400 MHZ, CDCl$_3$) δ 7.92-7.94 (m, 2H), 7.80-7.83 (m, 2H), 6.07-5.92 (m, 1H), 4.47 (dd, J=12.7, 4.3 Hz, 1H), 4.21-3.82 (m, 3H), 3.32-3.04 (m, 2H), 2.99-1.30 (m, 14H).

Example 38 to 39 were performed according to the operation of example 37, using GJD23 and GJD24 as raw materials and obtaining the target product via oxidative dehydrogenation reaction. Examples of results obtained are as follows:

| Example | yields | compound | (HR)MS-ESI and $^1$H NMR |
|---|---|---|---|
| 38 | 20% | GJD23 | HRMS-ESI: m/z calcd for $C_{23}H_{26}N_4O_3$: 406.2205, found [M+H]$^+$ 407.2085. |
| 39 | 34% | GJD24 | HRMS-ESI: m/z calcd for $C_{24}H_{27}N_3O_3$: 405.2052, found [M+H]$^+$ 406.2130. |

Example 40: Synthesis of Compound GJD46

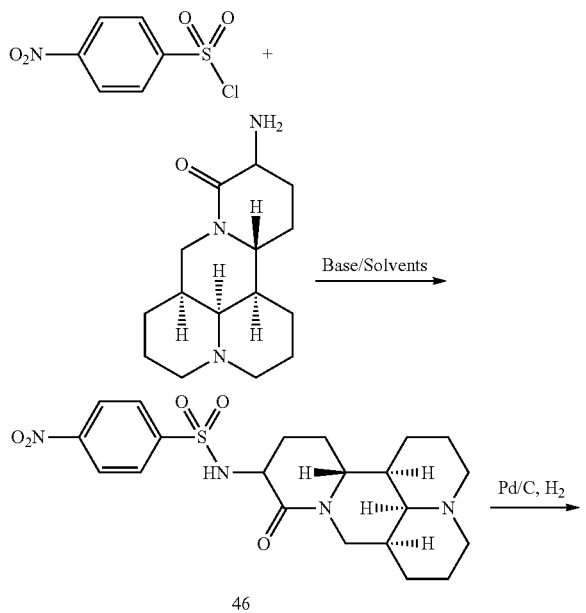

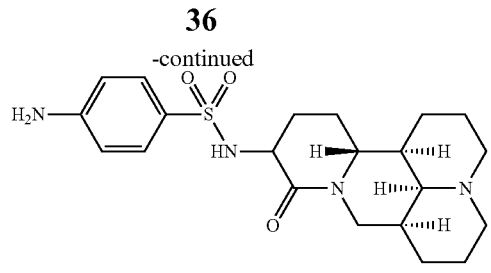

GJD46

Step 1: Synthesis of Intermediate 46

To a stirred solution of 14-amino-matrine (131 mg, 0.5 mmol) and triethylamine (75 mg, 0.75 mmol) in dichloromethane (10 mL) was slowly added p-nitrobenzene sulfonyl chloride (110 mg, 0.5 mmol) and continued to react for 1 to 2 h under ice-bath. After the reaction was completed (monitored by TLC), 25 ml of water was added, and extracting with dichloromethane (25 mL×2). The combined organic phase was sequentially washed with saturated brine, dried over anhydrous sodium sulfate, and filtered. The resulting filtrate was evaporated and purified by a basic alumina column chromatography ($V_{ethyl\ acetate}$: $V_{petroleum\ ether}$=1:2 to 1:1) to give the compound 46 (170 mg, yield 76%). MS-ESI [M+H]$^+$449.2.

Step 2: Synthesis of GJD46

To a stirred solution of compound 46 (45 mg, 0.1 mmol) in methanol (1 mL) was added 10% Pd/C, and the resulting mixture was heated to 70° C. under H$_2$ (50 Psi) atmosphere for 48 hours. After the reaction was completed (monitored by TLC), filtered, and the filtrate was evaporated to give GJD46 (32 mg, 78%). HRMS-ESI: m/z calcd for $C_{21}H_{30}N_4O_3$: 418.2039, found [M+H]$^+$419.2116. $^1$H NMR (400 MHZ, DMSO-d$_6$) δ 7.59-7.52 (m, 1H), 7.45 (d, J=8.7 Hz, 2H), 6.55 (d, J=8.7 Hz, 2H), 5.91 (s, 2H), 4.70-4.53 (m, 1H), 4.27 (dd, J=13.0, 4.4 Hz, 1H), 3.95 (td, J=10.6, 5.4 Hz, 1H), 3.21 (t, J=12.9 Hz, 1H), 2.92-2.72 (m, 2H), 2.60-2.46 (m, 1H), 2.38-2.30 (m, 1H), 2.05-1.87 (m, 5H), 1.78-1.37 (m, 10H).

Example 41 to 46 were performed according to the operation of example 40. The results of the obtained examples are as follows:

| Example | yields | compound | (HR)MS-ESI and $^1$H NMR |
|---|---|---|---|
| 41 | 90% | GJD02 | HRMS-ESI: m/z calcd for $C_{23}H_{28}N_4O_3$: 408.2161, found [M+H]$^+$ 409.2240. $^1$H NMR (400 MHz, CDCl$_3$) δ 7.36-7.30 (m, 1H), 7.07 (d, J = 7.1 Hz, 1H), 6.81 (d, J = 8.3 Hz, 1H), 5.28 (brs, 2H), 4.70 (dd, J = 11.4, 6.7 Hz, 1H), 4.30 (dd, J = 12.5, 4.2 Hz, 1H), 4.16-4.10 (m, 1H), 3.21 (t, J = 12.5 Hz, 1H), 2.96-2.75 (m, 2H), 2.48-1.84 (m, 7H), 1.81-1.34 (m, 10H). |
| 42 | | GJD18 | MS-ESI [M+H]$^+$ 409.2 (409.2). |
| 43 | 91% | GJD27 | HRMS-ESI: m/z calcd for $C_{23}H_{28}N_4O_3$: 408.2161, found [M+H]$^+$ 409.2240. $^1$H NMR (400 MHz, CDCl$_3$) δ 7.36-7.30 (m, 1H), 7.07 (d, J = 7.1 Hz, 1H), 6.81 (d, J = 8.3 Hz, 1H), 5.24 (brs, 2H), 4.72-4.63 (m, 1H), 3.80-3.61 (m, 1H), 3.58-3.45 (m, 1H), 3.30-3.12 (m, 1H), 2.96-2.89 (m, 2H), 2.89-2.80 (m, 1H), 2.63-2.05 (m, 4H), 2.01-1.65 (m, 4H), 1.62-1.48 (m, 6H), 1.35-1.04 (m, 2H). |
| 44 | 94% | GJD35 | HRMS-ESI: m/z calcd for $C_{23}H_{30}N_4O_2$: 394.2369, found [M+H]$^+$ 395.2448; $^1$H NMR (300 MHz, CDCl$_3$) δ 7.10-7.06 (m, 1H), 6.80-6.66 (m, 2H), 4.89-4.51 (m, 5H), 4.33-4.18 (m, 1H), 4.07-3.84 (m, 1H), 3.20-3.10 (m, 1H), 2.86-2.74 (m, 2H), 2.33-2.20 (m, 2H), 2.08-1.86 (m, 5H), 1.76-1.36 (m, 10H). |
| 45 | 96% | GJD41 | MS-ESI [M+H]$^+$ 395.2 (395.2); $^1$H NMR (400 MHz, DMSO-d$_6$) 7.24-6.81 (m, 3H), 5.38 (s, 2H), 4.89-4.57 (m, 1H), 4.43-4.18 (m, 3H), 4.07-3.84 (m, 1H), 3.22-3.10 (m, 1H), 2.86-2.74 (m, 2H), 2.33-2.20 (m, 2H), 2.08-1.86 (m, 5H), 1.76-1.36 (m, 10H). |
| 46 | 86% | GJD43 | MS-ESI [M+H]$^+$ 395.2 (395.2). |

Example 47: Synthesis of Compounds GJD47 and GJD48

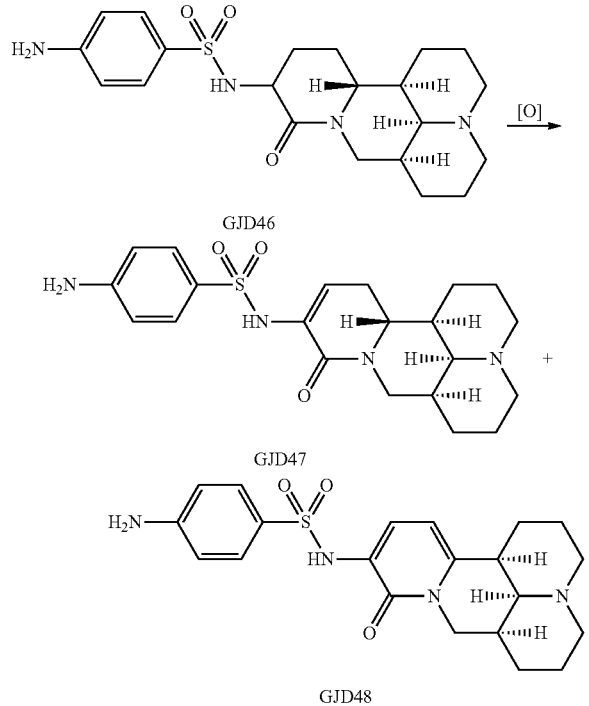

GJD46 (210 mg, 0.5 mmol) and DDQ (230 mg, 1 mmol) were added to chlorobenzene solution (10 mL), and the resulting mixture was heated to 120° C. for 48 h under nitrogen atmosphere. After the reaction was completed (monitored by TLC), sodium sulfite (252 mg, 2 mmol) was added and continue to stir for 1 hour at room temperature, then filtered. The obtained filtrate is evaporated and purified by a basic alumina column chromatography ($V_{chloroform}$:$V_{methanol}$=60:1~20:1) to give compounds GJD47 and GJD48. GJD47, 58 mg, yield 28%. $^1$H NMR (400 MHZ, DMSO-$d_6$) δ 7.92-7.83 (m, 1H), 7.49 (d, J=8.7 Hz, 2H), 6.59 (d, J=8.7 Hz, 2H), 6.09-5.93 (m, 3H), 4.45 (dd, J=12.7, 4.3 Hz, 1H), 4.21-3.83 (m, 3H), 3.32-3.05 (m, 2H), 2.99-1.31 (m, 14H). GJD47, 33 mg, yield 16%. HRMS-ESI: m/z calcd for $C_{21}H_{26}N_4O_3S$: 414.1726, found [M+H]$^+$415.1790.

Example 48: Synthesis of Compound GJD49

To a stirred solution of 14-amino-matrine (26 mg, 0.1 mmol) in 1,4-dioxane (1 mL) methyl was added 2-aminobenzoate (15 mg, 0.1 mmol) under $N_2$ atmosphere, and the resulting mixture heated to reflux for overnight. After the reaction was completed, water (50 mL) was added and extracting with ethyl acetate (2×50 mL), the combined organic phase was washed with saturated brine, dried over anhydrous sodium sulfate, concentrated, and pyrified by conventional silica gel column chromatography ($V_{ethyl\ acetate}$:$V_{petroleum\ ether}$=1:4 to 1:1) to give GJD49 (27 mg, yield 71%). HRMS-ESI: m/z calcd for $C_{22}H_{30}N_4O_2$: 382.2369, found [M+H]$^+$383.2445; 1H NMR (400 MHZ, DMSO-$d_6$) δ 8.49-8.41 (m, 1H), 7.49 (dd, J=8.2, 1.3 Hz, 1H), 7.14 (ddd, J=8.2, 7.1, 1.3 Hz, 1H), 6.68 (dd, J=8.2, 1.3 Hz, 1H), 6.50 (ddd, J=8.2, 7.1, 1.3 Hz, 1H), 6.42 (s, 2H), 4.70-4.53 (m, 1H), 4.27 (dd, J=13.0, 4.4 Hz, 1H), 3.95 (td, J=10.6, 5.4 Hz, 1H), 3.22 (t, J=12.9 Hz, 1H), 2.91-2.72 (m, 2H), 2.60-2.31 (m, 2H), 2.04-1.87 (m, 5H), 1.77-1.36 (m, 10H).

Example 49: Synthesis of Compound GJD51

To a stirred solution acetylsalicylic acid (18 mg, 0.1 mmol), EDCl (38 mg, 0.2 mmol), and DMAP (24 mg, 0.2 mmol) in DMF solution (1 mL) was added 14-amino-matrine (26 mg, 0.1 mmol) under ice-bath, and the resulting mixture was reacted at room temperature for overnight. After the reaction was completed, water (5 mL) was added and extracting with ethyl acetate (2×5 ml). The combined organic phase was washed with saturated brine, dried over anhydrous sodium sulfate, concentrated and purified by conventional silica gel column chromatography ($V_{ethyl\ acetate}$:$V_{petroleum\ ether}$=1:4 to 1:1) to give GJD51 (32 mg, yield 71%). HRMS-ESI: m/z calcd for $C_{24}H_{31}N_3O_4$: 425.2315, found [M+H]$^+$426.2390; 1H NMR (400 MHZ, DMSO-$d_6$) δ 8.49-8.42 (m, 1H), 7.67-7.62 (m, 1H), 7.55-7.50 (m, 1H), 7.38-7.32 (m, 1H), 7.22-7.18 (m, 1H), 4.70-4.53 (m, 1H), 4.29 (dd, J=13.0, 4.4 Hz, 1H), 3.95 (td, J=10.6, 5.4 Hz, 1H), 3.21 (t, J=12.9 Hz, 1H), 2.90-2.72 (m, 2H), 2.61-2.46 (m, 1H), 2.39-1.87 (m, 9H), 1.76-1.34 (m, 10H).

Examples 50 to 56 were performed according to the operation of example 49, and various commercially available substituted carboxylic acids were used as substrates to react with 14-aminomatrine to give GJD50 to GJD57. The results of the obtained examples are as follows:

| Example | yields | compound | (HR)MS-ESI and $^1$H NMR |
|---|---|---|---|
| 50 | 84% | GJD50 | HRMS-ESI: m/z calcd for $C_{22}H_{29}N_3O_3$: 383.2209, found [M+H]$^+$ 384.2280. |
| 51 | 81% | GJD52 | HRMS-ESI: m/z calcd for $C_{27}H_{35}F_2N_3O_4$: 503.2596, found [M+H]$^+$ 504.2670. $^1$H NMR (400 MHz, DMSO-$d_6$) δ 8.49-8.41 (m, 1H), 7.31-7.25 (m, 2H), 7.06 (d, J = 8.1 Hz, 1H), 6.62 (t, J = 14.1 Hz, 1H), 4.84-4.56 (m, 1H), 4.30 (dd, J = 13.0, 4.4 Hz, 1H), 3.98-3.86 (m, 3H), 3.22 (t, J = 12.9 Hz, 1H), 2.92-2.73 (m, 2H), 2.60-2.46 (m, 1H), 2.38-2.30 (m, 1H), 2.08-1.36 (m, 15H), 1.31-1.26 (m, 1H), 0.66 (d, J = 7.2 Hz, 2H), 0.38 (d, J = 4.5 Hz, 2H). |
| 52 | 89% | GJD53 | HRMS-ESI: m/z calcd for $C_{28}H_{39}N_3O_4$: 481.2941, found [M+H]$^+$ 482.3015. $^1$H NMR (400 MHz, DMSO-$d_6$) δ 8.49-8.42 (m, 1H), 7.46-7.38 (m, 2H), 6.97 (d, J = 8.4 Hz, 1H), 4.84-4.56 (m, 2H), 4.31 (dd, J = 13.0, 4.4 Hz, 1H), 3.95-3.82 (m, 4H), 3.21 (t, J = 12.9 Hz, 1H), 2.90-2.72 (m, 2H), 2.61-2.46 (m, 1H), 2.38-2.31 (m, 1H), 2.04-1.36 (m, 23H). |

-continued

| Example | yields | compound | (HR)MS-ESI and $^1$H NMR |
|---|---|---|---|
| 55 | 92% | GJD54 | HRMS-ESI: m/z calcd for $C_{25}H_{35}N_3O_4$: 441.2628, found [M+H]$^+$ 442.2700. |
| 54 | 86% | GJD55 | HRMS-ESI: m/z calcd for $C_{22}H_{28}ClN_3O_3$: 417.1819, found [M+H]$^+$ 418.1890. |
| 55 | 85% | GJD56 | HRMS-ESI: m/z calcd for $C_{28}H_{31}F_2N_3O_3$: 495.2333, found [M+H]$^+$ 496.2410. $^1$H NMR (400 MHz, DMSO-$d_6$) δ 8.49-8.42 (m, 1H), 7.92 (s, 1H), 7.63 (d, J = 8.4 Hz, 1H), 7.46-7.30 (m, 2H), 7.02-6.93 (m, 2H), 4.84-4.56 (m, 1H), 4.30 (dd, J = 13.0, 4.2 Hz, 1H), 3.97 (td, J = 10.6, 5.4 Hz, 1H), 3.21 (t, J = 12.9 Hz, 1H), 2.92-2.73 (m, 2H), 2.60-2.43 (m, 1H), 2.38-2.31 (m, 1H), 2.07-1.87 (m, 5H), 1.76-1.34 (m, 10H). |
| 56 | 91% | GJD57 | HRMS-ESI: m/z calcd for $C_{28}H_{32}FN_3O_3$: 477.2428, found [M+H]$^+$ 478.2500. |

Example 57 Synthesis of Compound GJD58

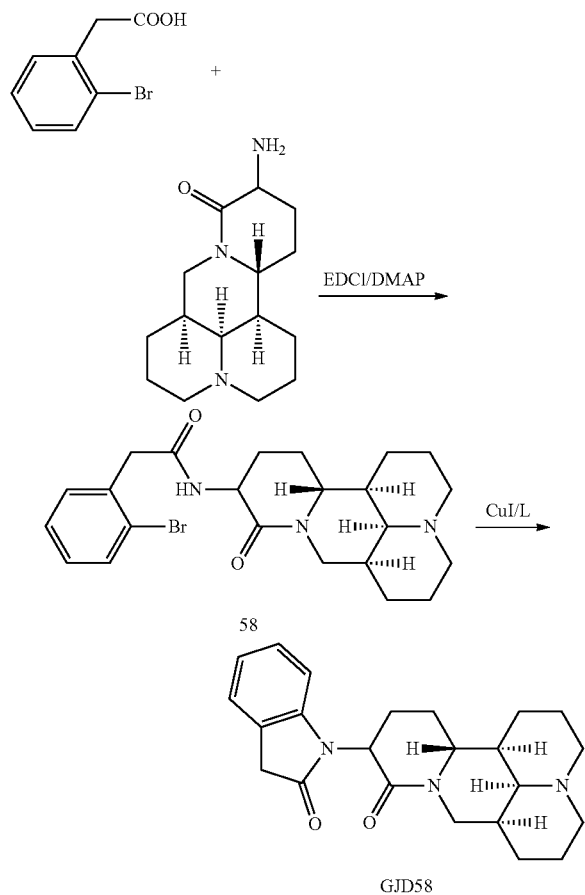

Step 1. To a stirred solution of 2-bromophenylacetic acid (215 mg, 1 mmol), EDCl (380 mg, 2 mmol), and DMAP (242 mg, 2 mmol) in DMF (5 mL) was added 14-aminomatrine (263 mg, 1 mmol) under ice-bath, and the resulting mixture was warmed to room temperature and stirred for overnight. After the reaction was completed, water (20 mL) was added and extracting with ethyl acetate (2×10 ml). The combined organic phase was washed with saturated brine, dried over anhydrous sodium sulfate, concentrated and purified by conventional silica gel column chromatography ($V_{ethyl\ acetate}:V_{petroleum\ ether}$=1:4 to 1:1) to give intermediate 58. HRMS-ESI: m/z calcd for $C_{23}H_{30}BrN_3O_2$: 459.1521, found [M+H]$^+$460.1598.

Step 2. Compound 58 (46 mg, 0.1 mmol), CuI (2 mg, 0.01 mmol), glycine (7 mg, 0.1 mmol), and cesium carbonate (65 mg, 0.2 mmol) were added to DMF solution and reacted at 130° C. for overnight under nitrogen atmosphere. After the reaction was completed, water (5 mL) was added and extracting with ethyl acetate (2×5 ml). The combined organic phase was washed with saturated brine, dried over anhydrous sodium sulfate, concentrated and purified by conventional silica gel column chromatography ($V_{ethyl\ acetate}:V_{petroleum\ ether}$=1:4 to 1:1) to give GJD58. HRMS-ESI: m/z calcd for $C_{23}H_{29}N_3O_2$: 379.2260, found [M+H]$^+$380.2338. $^1$H NMR (400 MHZ, CDCl$_3$) δ 7.26-7.21 (m, 2H), 7.07-6.98 (m, 2H), 4.68-4.34 (m, 2H), 3.98-3.58 (m, 3H), 3.22 (t, J=12.9 Hz, 1H), 2.92-2.73 (m, 2H), 2.60-2.46 (m, 1H), 2.38-2.31 (m, 1H), 2.07-1.86 (m, 5H), 1.75-1.36 (m, 10H).

Examples 58 to 60 were performed according to the operation of example 57, and various commercially available substituted o-bromophenylacetic acid were used as substrates to react with 14-aminomatrine or 14-amino sophoridine to give compounds GJD59 to GJD61, respectively. The results of the obtained examples are as follows:

| Example | yields | compound | (HR)MS-ESI and $^1$H NMR |
|---|---|---|---|
| 58 | 84% | GJD59 | HRMS-ESI: m/z calcd for $C_{23}H_{28}FN_3O_2$: 397.2166, found [M+H]$^+$ 398.2240. |
| 59 | 81% | GJD60 | HRMS-ESI: m/z calcd for $C_{23}H_{29}N_3O_2$: 379.2260, found [M+H]$^+$ 380.2342. |
| 60 | 73% | GJD61 | HRMS-ESI: m/z calcd for $C_{23}H_{28}FN_3O_2$: 397.2166, found [M+H]$^+$ 398.2243. |

Example 61 Synthesis of Compound GJD62

Example 69: Synthesis of Compound GJD63

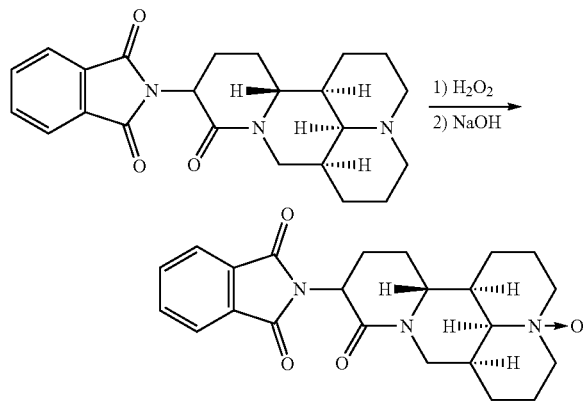

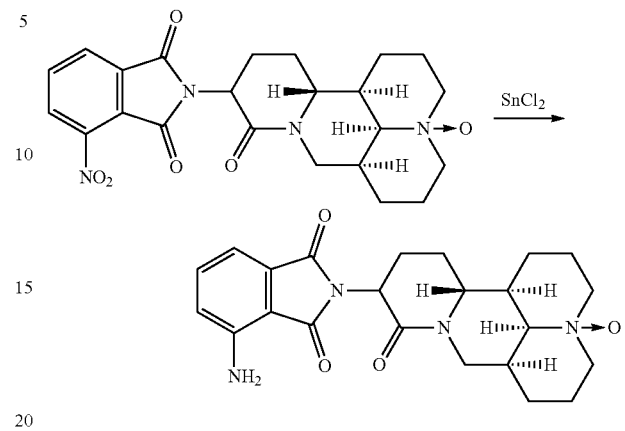

To a stirred solution of GJD01 (79 mg, 0.1 momol) in tetrahydrofuran (2 mL) was added 0.2 mL of 30% $H_2O_2$, and the resulting mixture was stirred at 50~60° C. for 1 h. After the reaction was completed (monitored by TLC), 5% NaOH solution (3 mL) was added and continued to stir at room temperature for 2 hours, after that, the reaction solution was neutralized with 1N dilute hydrochloric acid. The reaction solution was concentrated and redissolved with acetone and filtered to remove inorganic salts. The obtained filtrate was evaporated and purified by basic alumina column chromatography ($V_{chloroform}:V_{methanol}$=80:1 to 40:1) to give the compound of example 81 GJD62 (52 mg, yield 63%). MS-ESI $[M+H]^+$410.2 (410.2); 1H NMR (300 MHZ, $CD_3OD$) δ 8.09-7.52 (m, 4H), 4.70-3.92 (m, 4H), 3.38-2.86 (m, 5H), 2.72-1.26 (m, 14H).

Examples 62 to 68 were performed according to the operation of example 61, and the results obtained were as follows:

To a stirred solution of GJD66 (91 mg, 0.2 mmol) in 6N aqueous hydrochloric acid (5 mL) was slowly added $SnCl_2$ (190 mg, 1 mmol) under an ice-bath and N2 atmosphere, and the reaction temperature was raised to 60° C. and stirred for overnight. After the reaction was completed, the pH was adjusted with saturated sodium carbonate, and extracted with n-butanol, dried over anhydrous sodium sulfate, and filtered. The combined organic phase was concentrated and purified by alumina column chromatography ($V_{chloroform}$: $V_{methanol}$=40:1 to 20:1) to give the target compound GJD63 (39 mg, yield 46%). HRMS-ESI: m/z calcd for $C_{23}H_{28}N_4O_4$: 424.2111, found $[M+H]^+$425.2180. $^1$H NMR (400 MHZ, $CD_3OD$) δ 7.72-6.90 (m, 3H), 4.70-3.91 (m, 4H), 3.35-2.83 (m, 5H), 2.73-1.25 (m, 14H).

Examples 70 to 72 were performed according to the operation of example 69, the results obtained are as follows:

| Example | yields | compound | (HR)MS-ESI and $^1$H NMR |
|---|---|---|---|
| 70 | 31% | GJD67 | HRMS-ESI: m/z calcd for $C_{23}H_{30}N_4O_3$: 410.2318, found $[M+H]^+$ 411.2390. |
| 71 | 52% | GJD71 | HRMS-ESI: m/z calcd for $C_{23}H_{28}N_4O_4$: 424.2111, found $[M+H]^+$ 425.2180. |

| Example | yields | compound | (HR)MS-ESI and $^1$H NMR |
|---|---|---|---|
| 62 | 71% | GJD64 | HRMS-ESI: m/z calcd for $C_{25}H_{30}N_4O_5$: 466.2216, found $[M+H]^+$ 467.2290. $^1$H NMR (300 MHz, $CD_3OD$) δ 8.80-7.51 (m, 3H), 4.72-3.91 (m, 4H), 3.34-2.85 (m, 5H), 2.76-1.30 (m, 17H). |
| 63 | 54% | GJD65 | HRMS-ESI: m/z calcd for $C_{23}H_{26}FN_3O_4$: 427.1907, found $[M+H]^+$ 428.1985. $^1$H NMR (300 MHz, $CD_3OD$) δ 7.92-7.49 (m, 3H), 4.70-3.96 (m, 4H), 3.35-2.85 (m, 5H), 2.74-1.27 (m, 14H). |
| 64 | 85% | GJD66 | HRMS-ESI: m/z calcd for $C_{23}H_{26}N_4O_6$: 454.1852, found $[M+H]^+$ 455.1931. $^1$H NMR (300 MHz, $CD_3OD_3$) δ 8.27-7.82 (m, 3H), 4.85-3.96 (m, 4H), 3.38-2.84 (m, 5H), 2.76 -1.32 (m, 14H). |
| 65 | 68% | GJD68 | HRMS-ESI: m/z calcd for $C_{24}H_{31}N_3O_3$: 409. 2365, found $[M+H]^+$ 410.2445. |
| 66 | 77% | GJD69 | HRMS-ESI: m/z calcd for $C_{23}H_{28}FN_3O_3$: 413.2115, found $[M+H]^+$ 414.2890. |
| 67 | 76% | GJD70 | HRMS-ESI: m/z calcd for $C_{23}H_{27}N_3O_4$: 409.2002, found $[M+H]^+$ 410.2082. |
| 68 | 82% | GJD72 | HRMS-ESI: m/z calcd for $C_{24}H_{31}N_3O_3$: 409.2365, found $[M+H]^+$ 410.2446. |

-continued

| Example | yields | compound | (HR)MS-ESI and $^1$H NMR |
|---|---|---|---|
| 72 | 37% | GJD73 | HRMS-ESI: m/z calcd for $C_{23}H_{30}N_4O_3$: 410.2318, found $[M+H]^+$ 411.2396. |

Example 73 Preparation of the Representative Compound GJD01 Hydrochloride

The compound GJD01 (40 mg, 0.1 mmol) in ethanol was slowly added to a solution of hydrochloric acid in ethanol (0.1 N, 1.2 mL) at room temperature, and the resulting mixture was stirred for 1 hour. After the reaction was completed, ether was added to the above solution in an ice bath and resulted in solid precipitation and filtered. The obtained solid was dried under reduced pressure to give the GJD01 hydrochloride solid (43 mg, yield 100%). MS-ESI $[M+H]^+$ 394.2 (394.2).

Effect Examples

Example 74. TNF-α Activity Inhibiting Assay

Methods: Peripheral blood from healthy volunteers was collected with EDTA anticoagulant tubes. After being diluted 5-fold with 1640 medium (Gibco, USA), the blood was added to 96-well cell culture plates (Costar, USA) and then treated with 10 μL solution of the compound of general formula (I) of the present invention in DMSO (Sigma, USA), the final concentration of the compound was 20 UM with the final concentration of DMSO was 0.2%. After incubation for 60 minutes in an incubator at 37° C. under 5% $CO_2$, 10 μL LPS (Sigma, USA) was added to the reaction system, and the final concentration was 10 ng/ml. After further culturing for 6 hours in the incubator at 37° C. under 5% $CO_2$, the supernatant was collected. The content of TNF-α was determined by ELISA (BD Biosciences, USA). Absorbance was detected at OD 450 nm with a microplate reader, with OD 650 nm as reference. The control, a solution containing 0.2% DMSO medium, was as 0% inhibition. Raw data and standard curves were recorded. The four-parameter drug inhibition curve was plotted by XL-fit software and the inhibition rate of each compound was calculated. The experimental results are shown in table 1.

TABLE 1

TNF-α inhibitory activity

| Compound | TNF-α inhibition rate (%) | Compound | TNF-α inhibition rate (%) | Compound | TNF-α inhibition rate (%) |
|---|---|---|---|---|---|
| GJD 01 | ≥50 | GJD 14 | >50 | GJD 49 | >50 |
| GJD 02 | >50 | GJD 18 | <50 | GJD 50 | >50 |
| GJD 03 | >50 | GJD 19 | <50 | GJD 52 | >50 |
| GJD 04 | >50 | GJD 22 | >50 | GJD 53 | >50 |
| GJD 05 | >50 | GJD 27 | >50 | GJD 54 | >50 |
| GJD 06 | >50 | GJD 28 | >50 | GJD 65 | ≥50 |
| GJD 07 | >50 | GJD 29 | >50 | GJD 66 | <50 |
| GJD 08 | >50 | GJD 30 | <50 | GJD 67 | <50 |
| GJD 09 | >50 | GJD 33 | >50 | GJD 71 | >50 |
| GJD 10 | ≥50 | GJD 35 | >50 | GJD 72 | >50 |
| GJD 11 | <50 | GJD 38 | >50 | Oxymatrine | <50 |
| GJD 12 | >50 | GJD 41 | >50 | Sophoridine | <50 |
| GJD 13 | >50 | GJD 44 | >50 | Matrine | <50 |

Example 75 the Tumor Cells Growth-Inhibitory Activity Assay

Using MTT method to determine the growth inhibition activity of the matrine compounds on Lovo, MGC-803, Mia-paca2, HpeG-2, A549, k562, and Panc-1 cells in vitro. Logarithmic growth phase of Lovo, MGC-803, Mia-paca2, HpeG-2, A549, k562, Panc-1 cells were inoculated into 96-well plates (purchased from Institute of Biochemical Cells, Chinese Academy of Sciences, and cultured according to conventional tumor cell culture methods) at a density of 4×104/mL and 180 μL/well; after the cells adhered to the wall, 20 μL of drug solution was added to each well and maintained the final drug concentrations were 0.1 μM, 1 μM, 10 μM, 50 μM, 100 μM respectively. After 48h, 5 mg/mL MTT solution was added (20 μL/well) and maintained in a $CO_2$ incubator for 3~4 h. After that, discarding the supernatant carefully, and DMSO was added (200 μL/well) when the residual liquid was air-dried, and shook for 0.5~1 h until the residual crystals was dissolved. The absorbance OD was measured at 492 nm by a microplate reader. GraphPad Prism 5 software was used to calculate the $IC_{50}$ value. The results are shown in table 2.

TABLE 2

The tumors growth-inhibitory activity of α-ketoamine compounds

| | Tumors growth-inhibitory activity ($IC_{50}$) | | | | | | |
|---|---|---|---|---|---|---|---|
| Compound | Lovo | MGC-803 | Mia-paca2 | HpeG-2 | k562 | A549 | Panc-1 |
| GJD 01 | B | C | C | B | B | B | C |
| GJD 02 | A | B | B | A | A | B | A |
| GJD 06 | B | C | B | A | B | B | B |
| GJD 07 | A | B | B | B | B | C | B |
| GJD 16 | B | B | B | A | B | C | C |
| GJD 24 | A | B | B | A | A | A | B |
| GJD 25 | B | C | C | B | B | B | C |
| GJD 34 | B | B | B | A | A | B | B |
| GJD 47 | B | C | C | B | B | B | C |
| GJD 52 | B | B | B | A | B | A | B |
| GJD 55 | B | C | B | A | B | A | B |
| GJD 66 | A | B | B | A | A | A | A |
| GJD 72 | B | B | B | A | A | B | A |
| M-3 | B | C | C | B | B | B | C |
| Matrine | B | C | C | B | C | C | C |

Note:
A: <50 μM; B: 50~00 μM; C: >100 μM

Example 76 the Matrine α-Ketoamine Compounds Activated Tumors Growth-Inhibitory Activity of NK Cells Logarithmic growth phase of Lovo, HpeG-2, A549, k562, Panc-1 cells were collected and seeded in a 6-well plate at a density of 5×10$^5$/mL and 2 mL/well separately. The experimental group was treated with 20 μM final drug concentration of GJDx compounds, and the control group was treated with an equal volume of RPMI1640 medium. The groups were cultured at 37° C., saturated humidity, 5% $CO_2$ for 48 h. After that, the cells of each group were collected, centrifuged and the supernatant was removed and resuspended in PBS at a density of 1×10$^6$/mL. Then 2 μL of CFSE stock solution (final concentration was 10 μM) was added into the cell suspension per 1 mL and cultured at 37° C. with 5% $CO_2$ for 30 min, and then added 5-10 times of the volume of 4° C. pre-chilled RPMI 1640 complete medium, and incubated on ice for 5 minutes, discarded the supernatant by centrifugation at 4° C., and wash the cells with fresh medium for 3 times. After that, mixing the labeled tumor cells and NK cells (the NK cell culture medium was a-MEM contained 1.5 g/L sodium bicarbonate, 12.5% fetal bovine serum, and 12.5% horse serum) according to the ratio of 5:1, the mixture cells was collected and washed with flow buffer twice after incubated for 4 hours, then 50 μg/mL PI was added, and incubated at room temperature for 15 minutes in the dark, and finally testing the percentage of $CFSE^+PI^+$ tumor cells on the flow cytometer.

TABLE 3

Anti-tumor activity of NK cells activated by the representative compounds

| Compound | Lovo inhibition rate (%) | HpeG-2 inhibition rate (%) | A549 inhibition rate (%) | k562 inhibition rate (%) | Panc-1 inhibition rate (%) |
|---|---|---|---|---|---|
| GJD 01 | ≥50 | >50 | >50 | <50 | <50 |
| GJD 02 | >50 | >50 | >50 | >50 | >50 |
| GJD 07 | >50 | >50 | <50 | >50 | >50 |
| GJD 15 | >50 | >50 | <50 | <50 | >50 |
| GJD 26 | >50 | >50 | >50 | >50 | >50 |
| GJD 31 | >50 | >50 | >50 | >50 | ≥50 |
| GJD 42 | >50 | >50 | >50 | <50 | <50 |
| GJD 51 | <50 | >50 | <50 | <50 | <50 |
| GJD 55 | <50 | <50 | <50 | <50 | >50 |
| GJD 63 | ≥50 | >50 | >50 | >50 | >50 |
| GJD 67 | <50 | >50 | >50 | >50 | <50 |
| GJD 72 | >50 | >50 | >50 | >50 | <50 |
| Matrine | <50 | <50 | <50 | <50 | <50 |

Example 77 In Vivo Evaluation of Anti-Tumor Activity of the Representative Compound GJD01

Experimental animal model: Male 42±2 days-old specific pathogen free (SPF) nude mice (weight, 23-27 g) were obtained from Shanghai Laboratory Animal Center. Logarithmic growth phase of A549 cells (Growth from 7 to 11 days, 2~5×10$^6$/mL) were subcutaneously implanted into the axilla region of mice. After incubating for 24 hours, the animals were randomized into 4 groups (6 mices in blank group, and 5 mices in each experiment group). Compound GJD01 and matrine were administered by intraperitoneal injection at a dose of 30 mg/kg once a day for 15 days; vinblastine sulfate 2 mg/kg was administered by tail vein injection every other day for 15 days.

Figure 2:
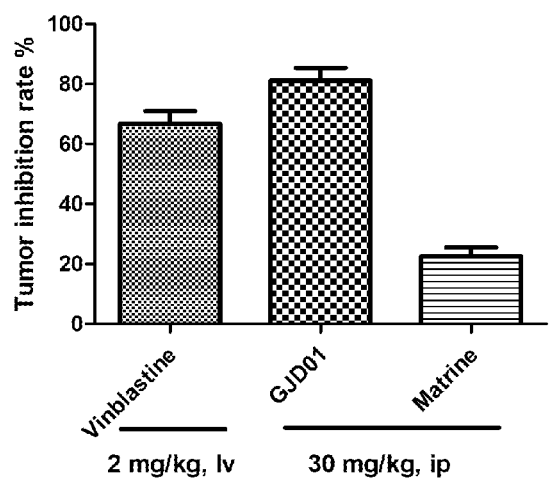
FIG. 2 is the tumor inhibition rate of nude mice model of A549 xenograft tumor.

Twenty-four hours after drug withdrawal, the animals were sacrificed, and recorded the body weight and tumor weight, the tumor inhibition rate was calculated according to the following formula with T test. Tumor inhibition rate IR (%)=(average tumor weight of the blank control group-average tumor weight of the treatment group)/average tumor weight of the blank control group×100%. The main criteria for evaluation of curative effect: tumor inhibition rate<40% was invalid; tumor inhibition rate≥40% was effective (p<0.05, acceptable error boundary level). The experimental results were shown in FIGS. 1 and 2.

What is claimed is:
1. A matrine α-ketoamine derivative having a structure of general formula (I), a pharmaceutically acceptable salt, a stereoisomer, or an isotopic compound thereof;

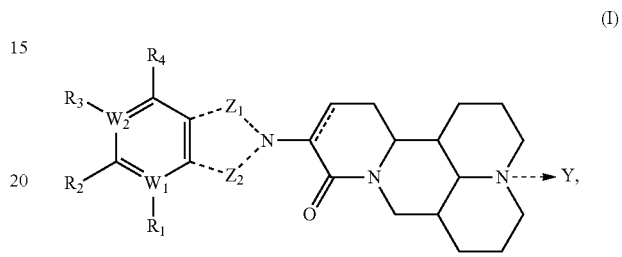

wherein each of $R_1$, $R_2$, $R_3$ and $R_4$ is independently selected from H, D, halogen, hydroxyl, amino, nitro, cyano, carboxyl, mercapto, ($C_0$-$C_8$) alkoxyformyl $C_1$-$C_8$ alkoxyl, $C_1$-$C_8$ alkanesulfonyl, ($C_1$-$C_8$) alkanesulfonamido, ($C_0$-$C_8$) alkylaminosulfonyl, ($C_1$-$C_8$) alkyl, halo ($C_1$-$C_8$) alkyl, halo ($C_1$-$C_8$) alkoxyl, ($C_0$-$C_8$) alkylethynyl, ($C_1$-$C_8$) alkoxyl, ($C_1$-$C_8$) alkylacyloxy, ($C_1$-$C_8$) alkoxyl ($C_1$-$C_8$) alkoxyl, ($C_1$-$C_8$) alkoxyl ($C_1$-$C_8$) alkyl, ($C_1$-$C_8$) alkylamino, ($C_0$-$C_8$) alkylamino ($C_1$-$C_8$) alkyl, aryl, aryl ($C_1$-$C_8$) alkylamino ($C_1$-$C_8$) alkyl, amidino, guanidino, arylsulfonamido, arylaminosulfonyl, benzoyl, aryl ($C_1$-$C_8$) alkylamino, aryl ($C_1$-$C_8$) alkylamido, ($C_1$-$C_8$) alkoxyformyl, ($C_1$-$C_8$) alkylamido, ($C_0$-$C_8$) alkylamino selenyl, ($C_0$-$C_8$) alkylamino formamido, ($C_0$-$C_8$) alkylamino formyl, ($C_1$-$C_8$) alkylaminoformyloxyl, arylaminoformamido, arylaminoformyl, aryl ($C_0$-$C_8$) alkylaminoformyl, arylaminoformyloxyl, or absent; wherein, the aryl groups of $R_1$, $R_2$, $R_3$ and $R_4$ described are phenyl or are phenyl which independently substituted with 1-4 halogen, hydroxy, nitro, cyano, amino, trifluoromethyl, carboxyl, ($C_1$-$C_8$) alkanesulfonamido, ($C_1$-$C_8$) alkyl, halo ($C_1$-$C_8$) alkoxyl, ($C_1$-$C_8$) alkoxyl groups;

Y is O or not exist;

$Z_1$ is selected from $SO_2$, C=O, C=NR$_5$, COCO, CH$_2$CO, CH(CH$_3$)CO, CH$_2$, CH(CH$_3$)$_2$, CH$_2$CH(CH$_3$)$_2$, or H;

$Z_2$ is selected from $SO_2$, C=O, C=NR$_5$, COCO, CH$_2$CO, CH(CH$_3$)CO, CH$_2$, CH(CH$_3$)$_2$, or CH$_2$CH(CH$_3$)$_2$;

wherein, $R_5$ is selected from H, ($C_1$-$C_8$) alkoxyl;

$W_1$ and/or $W_2$ are independently selected from N or C; wherein, when $W_1$ and/or $W_2$ is N, $R_1$ and $R_3$ are not exist;

Where bonds represented by "-----" is a chemical bond or not exist.

2. The matrine α-ketoamine derivatives having a structure of general formula (I), the pharmaceutically acceptable salt, the stereoisomer, or the isotopic compound thereof according to claim 1, wherein the compounds having structures of general formula (I-a) and/or (I-b):

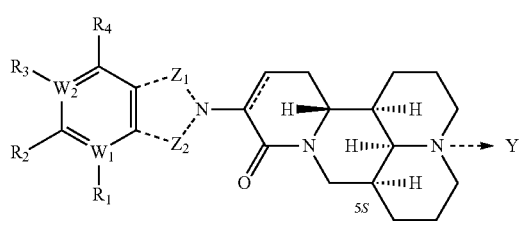

in the general formula (I-a) and (I-b), each of $R_1$, $R_2$, $R_3$ and $R_4$ is independently selected from H, D, halogen, hydroxyl, amino, nitro, cyano, carboxyl, mercapto, $(C_0$-$C_8)$ alkoxyformyl $C_1$-$C_8$ alkoxyl, $C_1$-$C_8$ alkanesulfonyl, $(C_1$-$C_8)$ alkanesulfonamido, $(C_0$-$C_8)$ alkylaminosulfonyl, $(C_1$-$C_8)$ alkyl, halo $(C_1$-$C_8)$ alkyl, halo $(C_1$-$C_8)$ alkoxyl, $(C_0$-$C_8)$ alkylethynyl, $(C_1$-$C_8)$ alkoxyl, $(C_1$-$C_8)$ alkylacyloxy, $(C_1$-$C_8)$ alkoxyl $(C_1$-$C_8)$ alkoxyl, $(C_1$-$C_5)$ alkoxyl $(C_1$-$C_8)$ alkyl, $(C_1$-$C_8)$ alkylamino, $(C_0$-$C_8)$ alkylamino $(C_1$-$C_8)$ alkyl, aryl, aryl $(C_1$-$C_8)$ alkylamino $(C_1$-$C_8)$ alkyl, amidino, guanidino, arylsulfonamido, arylaminosulfonyl, benzoyl, aryl $(C_1$-$C_8)$ alkylamino, aryl $(C_1$-$C_8)$ alkylamido, $(C_1$-$C_8)$ alkoxyformyl, $(C_1$-$C_8)$ alkylamido, $(C_0$-$C_8)$ alkylamino formamido, $(C_0$-$C_8)$ alkylamino formyl, $(C_1$-$C_8)$ alkylaminoformyloxyl, arylaminoformamido, arylaminoformyl, aryl $(C_0$-$C_8)$ alkylaminoformyl, arylaminoformyloxyl, or absent; wherein, the aryl groups of $R_1$, $R_2$, $R_3$ and $R_4$ described are phenyl or are phenyl which independently substituted with 1-4 halogen, hydroxy, nitro, cyano, amino, trifluoromethyl, carboxyl, $(C_1$-$C_8)$ alkanesulfonamido, $(C_1$-$C_8)$ alkyl, halo $(C_1$-$C_8)$ alkoxyl, $(C_1$-$C_8)$ alkoxyl groups;

Y is O or not exist;

$Z_1$ is selected from $SO_2$, C=O, $CH_2CO$, $CH(CH_3)CO$, $CH_2$, $CH(CH_3)_2$, $CH_2CH(CH_3)_2$, or H;

$Z_2$ is selected from $SO_2$, C=O, $CH_2CO$, $CH(CH_3)CO$, $CH_2$, $CH(CH_3)_2$, or $CH_2CH(CH_3)_2$;

$W_1$ and/or $W_2$ are independently selected from N or C; wherein, when $W_1$ and/or $W_2$ is N, $R_1$ and $R_3$ are not exist;

where bonds represented by "-----" is chemical bond or not exist.

3. The matrine α-ketoamine derivatives, the pharmaceutically acceptable salt, the stereoisomer, or the isotopic compound thereof according to claim 1, wherein the pharmaceutically acceptable salt is obtained by reacting the matrine α-ketoamine compound with an proper acid, and the acid can be hydrochloric acid, hydrobromic acid, sulfuric acid, phosphoric acid, acetic acid, citric acid, oxalic acid, malonic acid, salicylic acid, malic acid, fumaric acid, succinic acid, mandelic acid, ascorbic acid, maleic acid, tartaric acid, benzenesulfonic acid, methanesulfonic acid or isethionic acid.

4. A process for preparing the matrine α-ketoamine derivatives, the pharmaceutically acceptable salt, the stereoisomer, or the isotopic compound thereof according to claim 2, comprising:

a) the synthesis route for preparing matrine α-ketoamine compounds represented by general formula I-a and/or I-b;

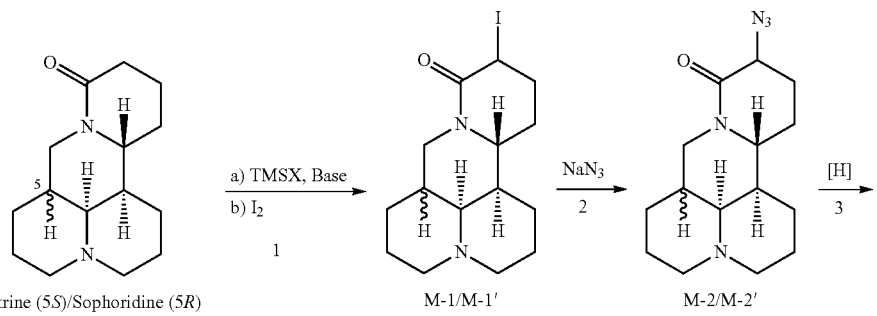

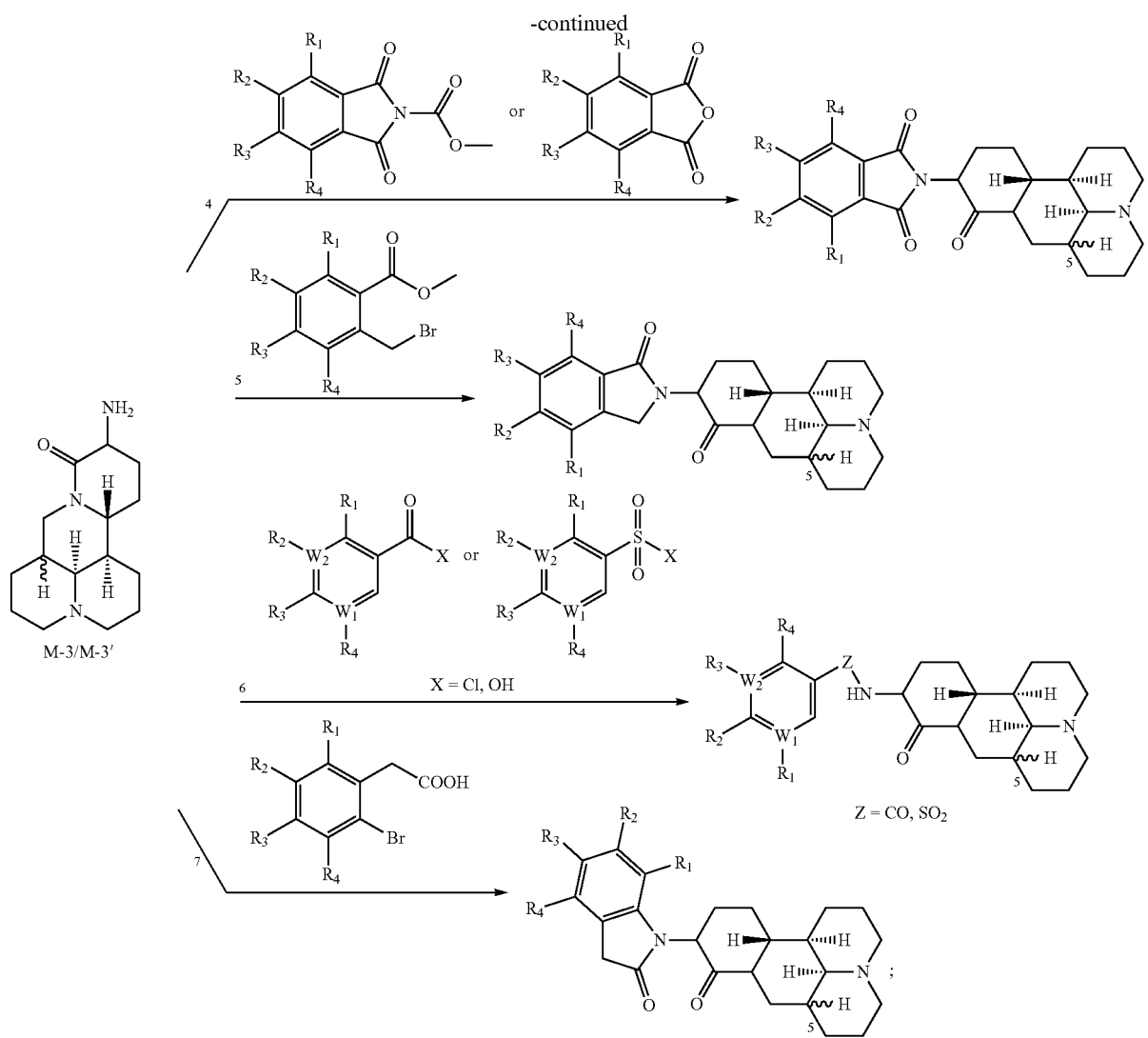
b) the synthesis method for preparing the amino substituted matrine α-ketoamine compounds represented by general formula I-a and/or I-b;
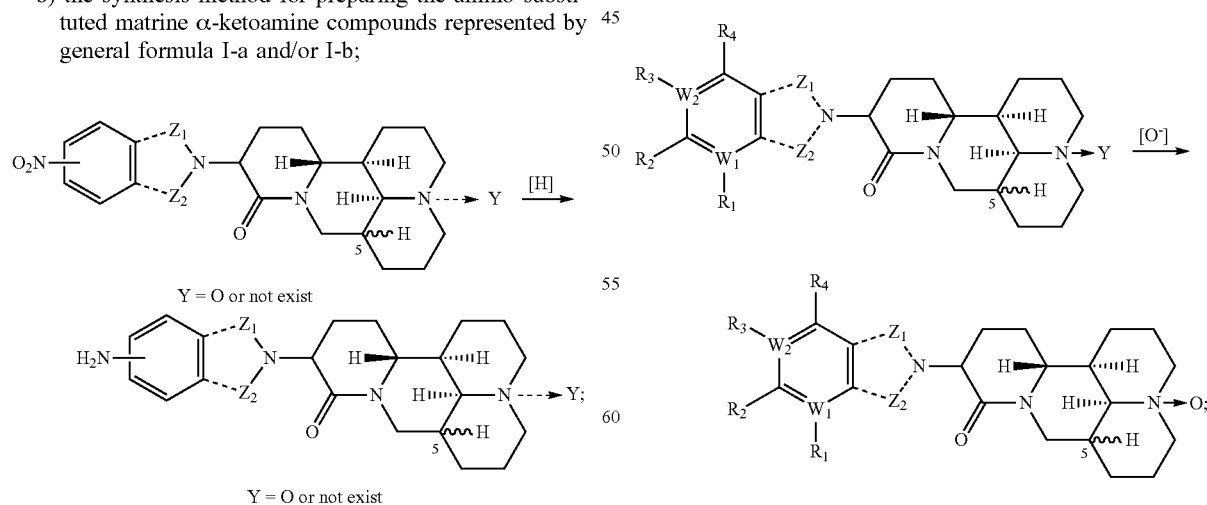
c) the synthesis method for preparing nitrogen oxides represented by general formula I-a and/or I-b;
d) the synthesis method for preparing 13,14-dehydromatrine α-ketoamine compounds represented by general formula I-a and/or I-b;

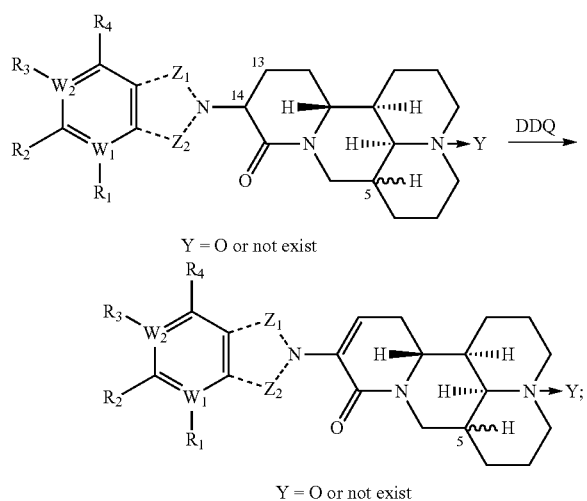

Y = O or not exist

Y = O or not exist the synthesis route a) for preparing the matrine α-ketoamine derivatives represented by general formula I-a and/or I-b, using matrine or sophoridine as raw materials, which can react with halogen at carbonyl alpha-site to afford the corresponding intermediate M-1 or M-1' (step 1), and then can obtain the azide intermediates M-2 or M-2' (step 2) via the $S_N2$ reaction, followed by a reduction reaction to form the key intermediates M-3 or M-3' (step 3) correspondingly, the key intermediates M-3 or M-3' can react with different N-formylmethyl phthalimides or phthalic anhydrides to afford substituted phthalimide matrine or sophoridine compounds respectively (step 4), and can also react with different alkoxyformyl benzyl bromide to afford substituted isoindolin-1-one matrine or sophoridine compounds respectively (step 5), as well as can react with aromatic formic acid or aromatic sulfonic acid to afford the substituted acyl (sulfonyl) matrine or sophoridine compounds respectively (step 6) moreover, M-3 and M-3' can react with different o-bromophenylacetic acid following by intramolecular cyclization to afford the substituted indolone matrine or sophoridine compounds (step 7), respectively;

the synthesis route b) for preparing amino substituents matrine α-ketoamine compounds having a structure of formulas I-a and I-b can be obtained by the reduction of the corresponding nitro-substituted compounds with the [H] reductive amination system;

the synthesis route c) for preparing matrine α-ketoamine nitrogen oxides having a structure of formulas I-a and I-b can be obtained by the peroxidation of the corresponding matrine α-ketoamine compounds with the [O] peroxidation system; and the synthesis route d) for preparing 13,14-dehydromatrine α-ketoamine compounds having a structure of formulas I-a and I-b can be obtained by oxidative dehydrogenation of the corresponding matrine α-ketoamine compounds, respectively.

5. A method of treating autoimmune diseases, neurological degenerative diseases, hematological tumors, solid tumors, myelofibrosis, and acute/chronic graft-versus-host response which are caused by the overexpression and/or abnormal expressions of TNF-α, comprising administering to a subject a therapeutically or prophylactically effective amount of a matrine α-ketoamine derivative of claim 1, a pharmaceutically acceptable salt, a stereoisomer, or an isotopic compound thereof.

6. A method of treating tumors and aging diseases which are caused by the immune disfunction of NK cells, comprising administering to a subject a therapeutically or prophylactically effective amount of a matrine α-ketoamine derivative of claim 1, a pharmaceutically acceptable salt, a stereoisomer, or an isotopic compound thereof.

7. A method of treating a disease, symptom or disorder caused by the overexpression of TNF-α and/or the immune disfunction of NK cells, wherein the method comprises administering to a subject a therapeutically or prophylactically effective amount of a substance selected from the group consisting of general formula (I) and the pharmaceutically acceptable salt thereof according to claim 1.

8. The method according to claim 5, wherein the autoimmune disease is rheumatoid arthritis, inflammatory bowel disease, diabetes, psoriasis, mandatory spondylitis, leprosy nodular erythema, lupus erythematosus, HBV, HCV, or HIV.

9. The method according to claim 5, wherein the neurological degenerative disease is Alzheimer's disease, dementia, Parkinson's disease, multiple sclerosis, Huntington's disease, amyotrophic lateral sclerosis (ALS), spinocerebellar ataxia (SCA), or pick's disease.

10. The method according to claim 5, wherein the hematological tumor is myelodysplastic syndrome, chronic lymphoblastic leukemia, multiple myeloma, mantle cell lymphoma, non-Hodgkin's lymphoma, chronic myelomonocytic leukemia, T-cell lymphoma, erythroid lymphoma, monocyte and monocyte leukemia, myeloid leukemia, myelofibrosis, Burkitt's lymphoma, Hodgkin's lymphoma, large cell lymphoma, or diffuse large B cell lymphoma.

11. The method according to claim 5, wherein the solid tumor is liver cancer, kidney cancer, gastric cancer, colon cancer, ovarian cancer, pancreatic cancer, prostate cancer, breast cancer, melanoma, papillary and follicular thyroid cancer, glioblastoma, gliosarcoma, malignant glioma, refractory plasmacytoma, ciliary body and chronic melanoma, iris melanoma, recurrent interocular melanoma and extraocular extended melanoma, brain tumor, meningioma, spinal cord tumor, thyroid cancer, non-small cell lung cancer, skin cancer, or stellate cell tumor.

12. The matrine α-ketoamine derivatives having a structure of general formula (I), the pharmaceutically acceptable salt, the stereoisomer, or the isotopic compound thereof according to claim 1, wherein the compounds having a structure of general formula (I) is selected from the group consisting of

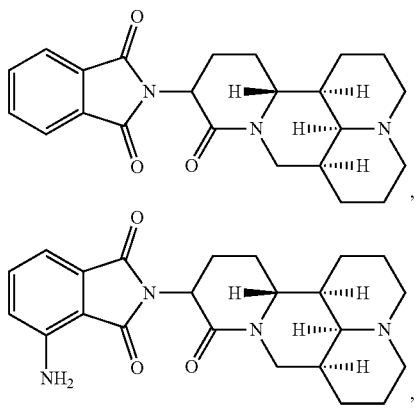

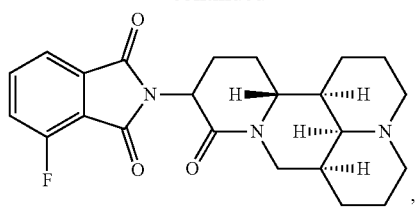,
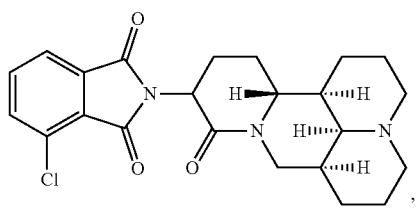,
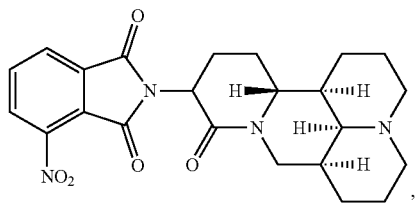,
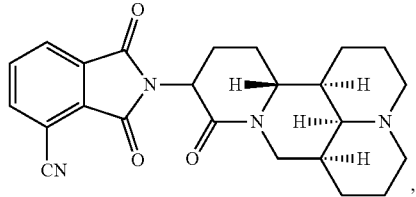,
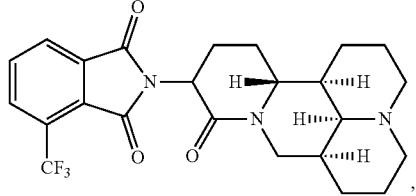,
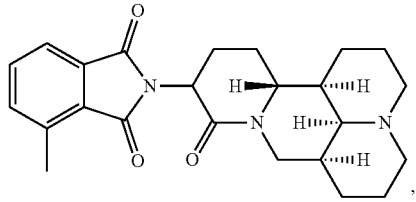,
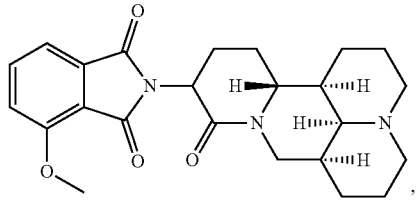,
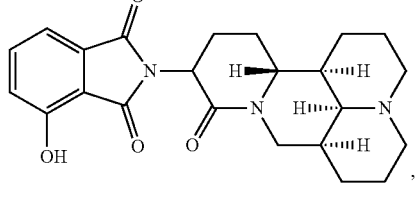,
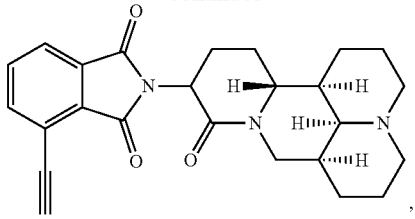,
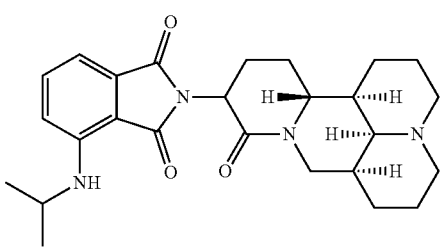,
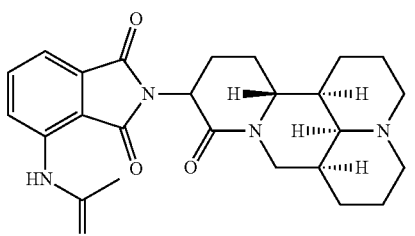,
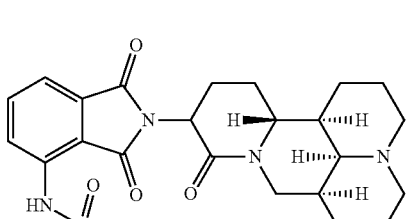,
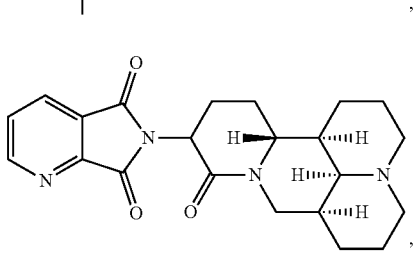,
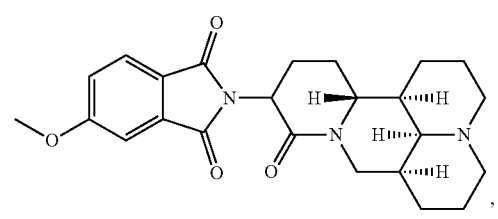,
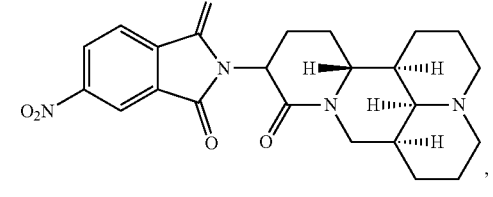, 55
-continued
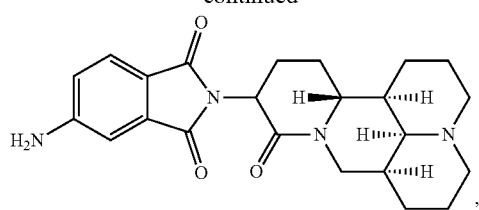
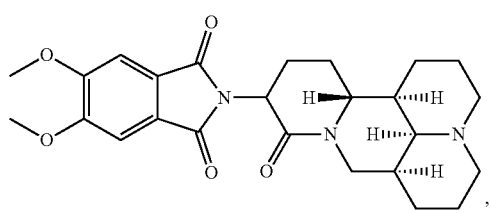
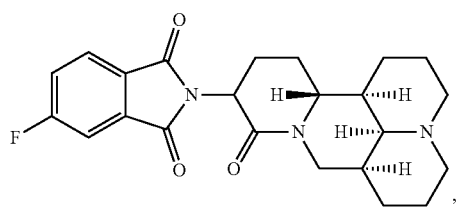
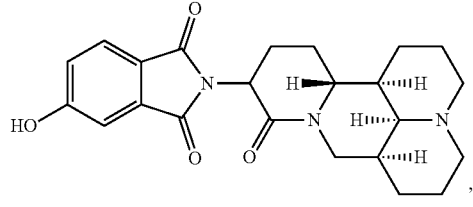
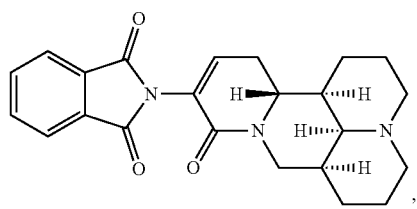
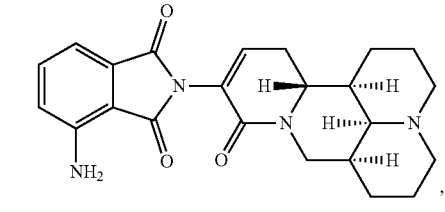
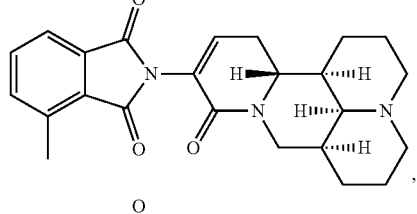
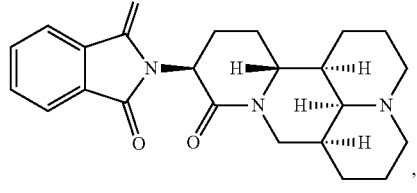
56
-continued
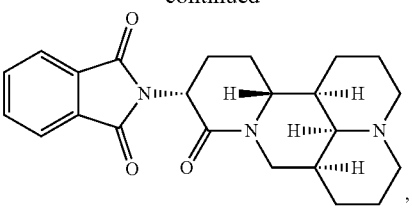
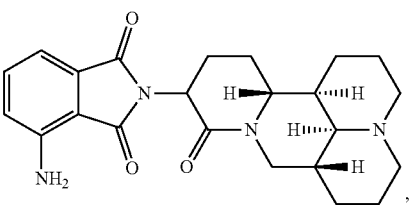
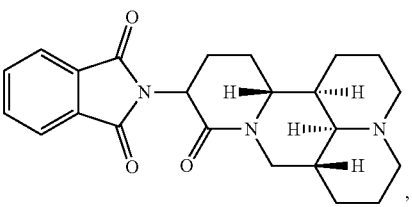
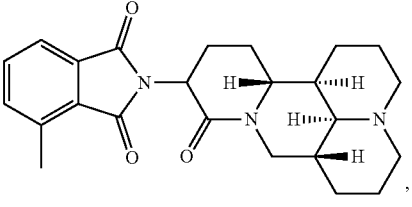
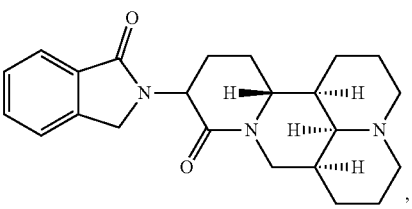
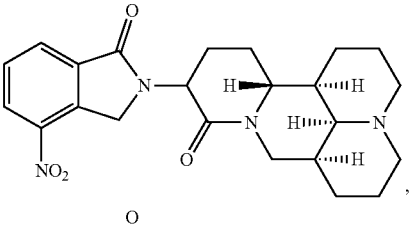
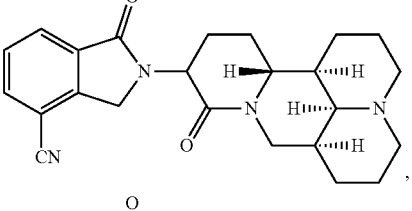
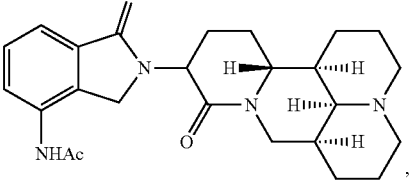

57 -continued

58 -continued

59
-continued
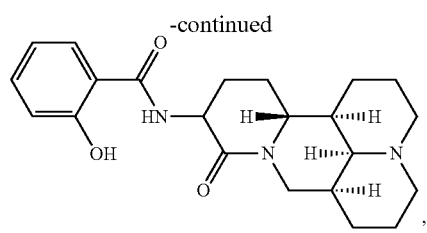
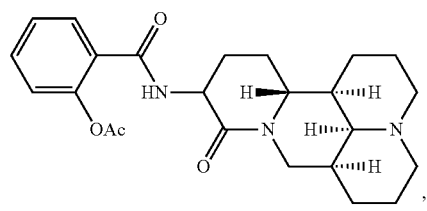
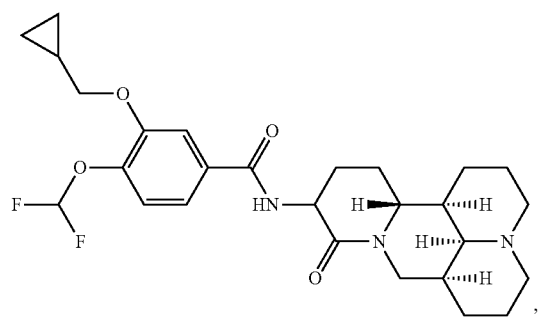
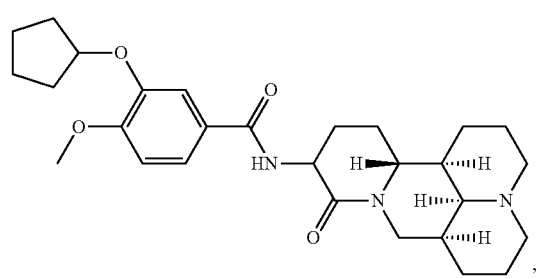
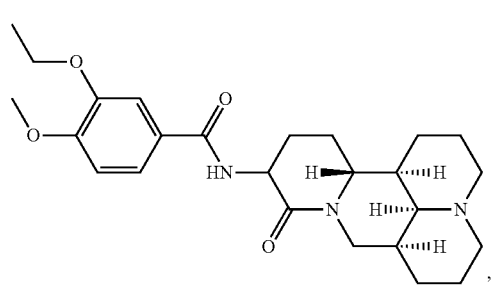
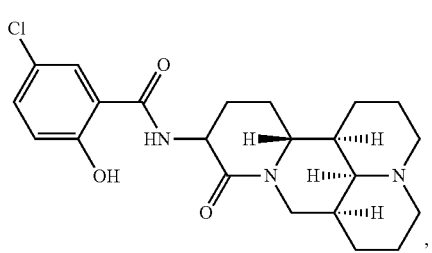
60
-continued
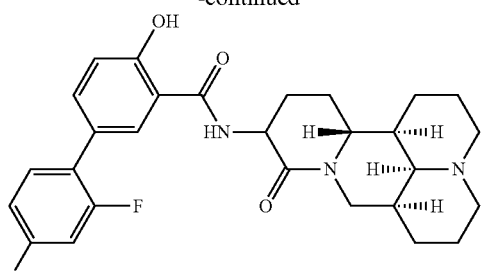
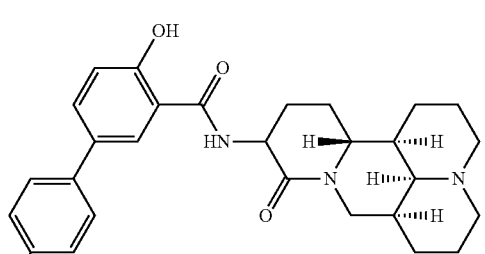
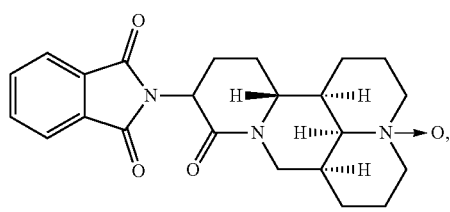
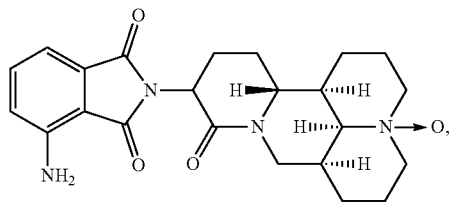
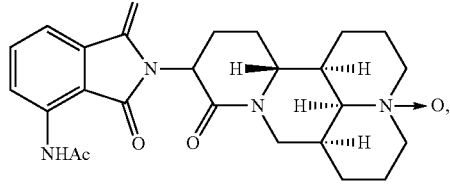
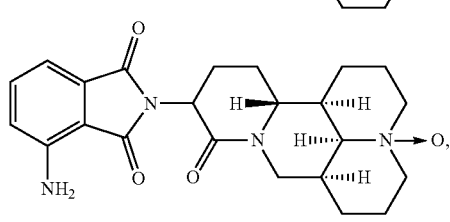

61
-continued
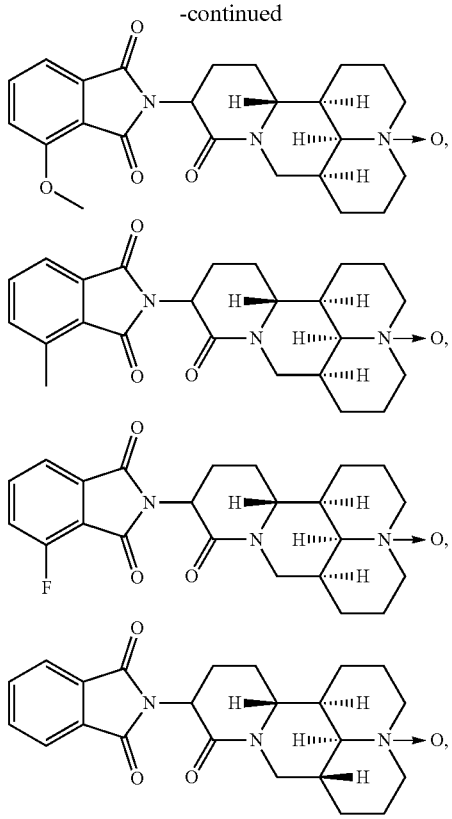
62
-continued
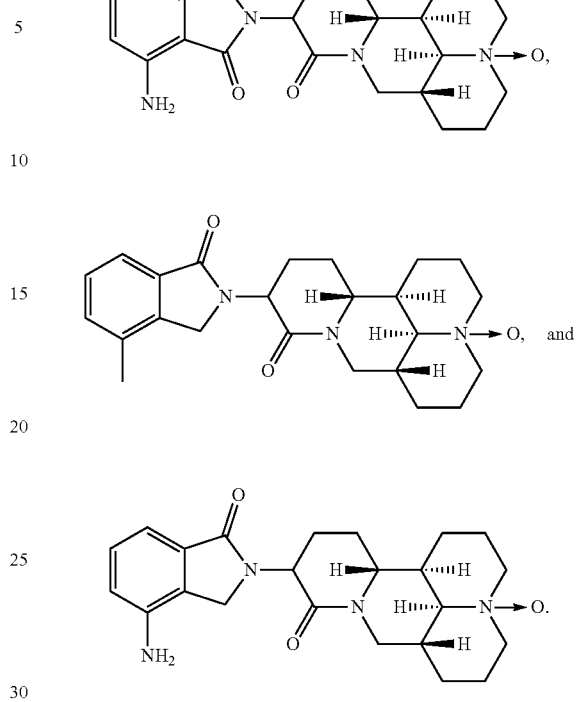
* * * * *